United States Patent
Kanayama et al.

(10) Patent No.: US 9,597,058 B2
(45) Date of Patent: Mar. 21, 2017

(54) ULTRASOUND DIAGNOSIS APPARATUS AND ULTRASOUND IMAGING METHOD

(71) Applicant: Toshiba Medical Systems Corporation, Otawara-shi (JP)

(72) Inventors: Yuko Kanayama, Nasushiobara (JP); Masahiko Yano, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 77 days.

(21) Appl. No.: 14/482,543

(22) Filed: Sep. 10, 2014

(65) Prior Publication Data

US 2015/0073275 A1 Mar. 12, 2015

(30) Foreign Application Priority Data

Sep. 11, 2013 (JP) .................. 2013-188776

(51) Int. Cl.
*A61B 8/00* (2006.01)
*A61B 8/08* (2006.01)
*G01S 7/52* (2006.01)

(52) U.S. Cl.
CPC ............ *A61B 8/5207* (2013.01); *A61B 8/469* (2013.01); *A61B 8/485* (2013.01); *A61B 8/5223* (2013.01); *A61B 8/56* (2013.01); *G01S 7/52042* (2013.01); *G01S 7/52077* (2013.01)

(58) Field of Classification Search
CPC ....... A61B 8/5207; A61B 8/469; A61B 8/485; A61B 8/5223; A61B 8/56; G01S 7/52077; G01S 7/52042

USPC .................................................. 600/437–469
See application file for complete search history.

(56) References Cited

U.S. PATENT DOCUMENTS

| | | | |
|---|---|---|---|
| 2012/0123262 A1* | 5/2012 | Xie ...................... | A61B 5/0048 600/438 |
| 2014/0100459 A1* | 4/2014 | Xu ...................... | A61B 17/2258 600/439 |
| 2016/0000398 A1* | 1/2016 | Raju ...................... | A61B 8/06 600/443 |
| 2016/0000411 A1* | 1/2016 | Raju ...................... | A61B 5/6842 600/443 |

* cited by examiner

*Primary Examiner* — Sanjay Cattungal
(74) *Attorney, Agent, or Firm* — Oblon, McClelland, Maier & Neustadt, L.L.P.

(57) ABSTRACT

An ultrasound diagnosis apparatus includes a transmitter, a generator, and an output controller. The transmitter transmits, from an ultrasound probe, push pulses that cause displacement of body tissue according to an acoustic radiation force and transmits, from the ultrasound probe, tracking pulses for observing the displacement of body tissue, which is caused according to the push pulses, in a given scanning area. The generator generates transmission area image data displaying a position to which the push pulses are transmitted. The output controller outputs the generated transmission area image data such that the transmission area image data is superimposed onto medical image data that contains the transmission area.

8 Claims, 15 Drawing Sheets

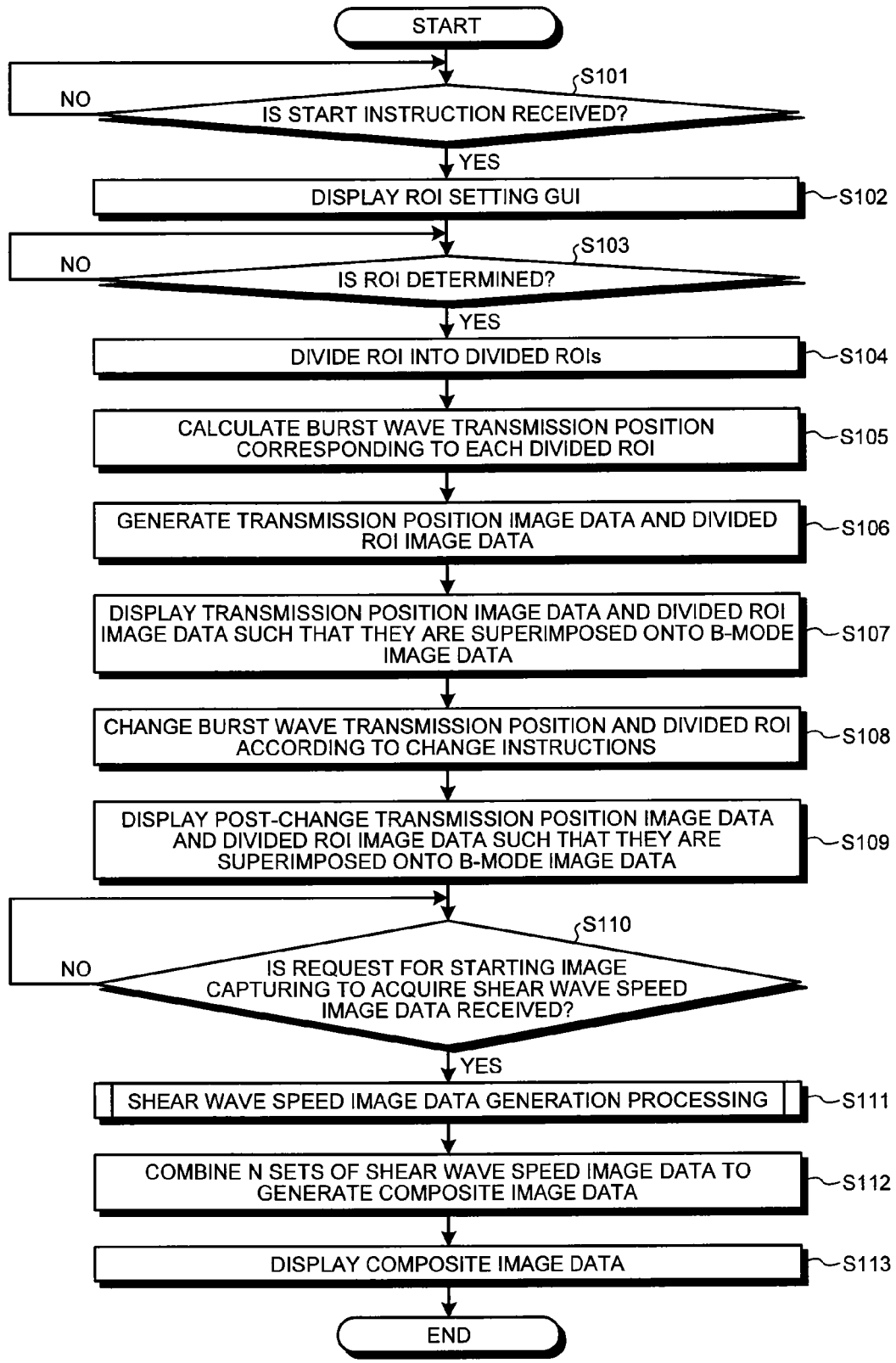

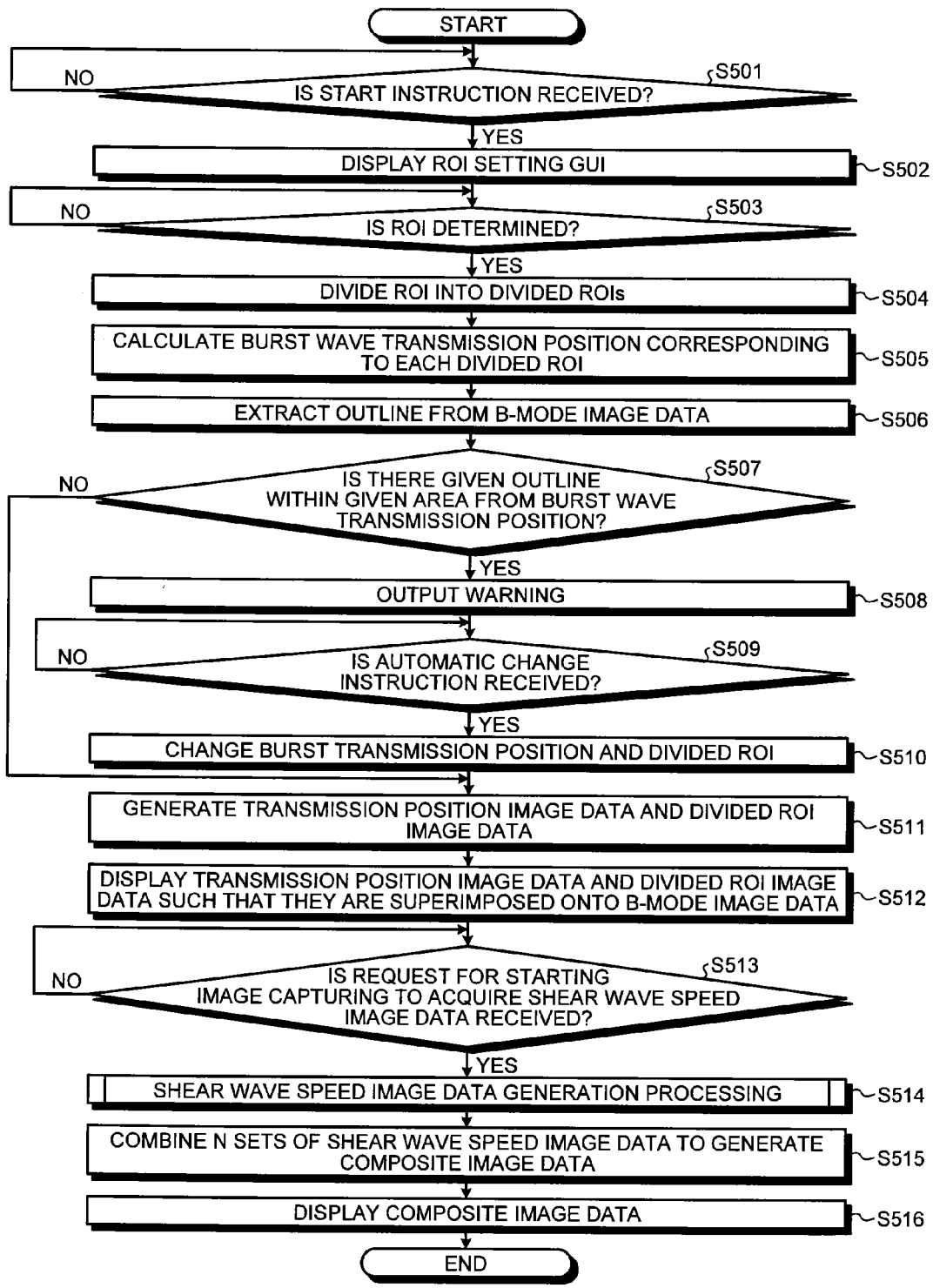

ULTRASOUND DIAGNOSIS APPARATUS AND ULTRASOUND IMAGING METHOD

CROSS-REFERENCE TO RELATED APPLICATIONS

This application is based upon and claims the benefit of priority from Japanese Patent Application No. 2013-188776, filed on Sep. 11, 2013, the entire contents of all of which are incorporated herein by reference.

FIELD

Embodiments described herein relate generally to an ultrasound diagnosis apparatus and an ultrasound imaging method.

BACKGROUND

Elastography is a known modality in which the hardness of body tissue is measured and the distribution of the measured hardnesses is then visualized. Elastography is used to diagnose diseases, such as liver cirrhosis, in which the hardness of body tissue changes according to the advancement of lesions. In elastography, there are two main methods to evaluate hardness, and in both methods the body tissue is displaced.

In the first method, the relative hardness of body tissue is visualized by using the magnitude of distortion at each point along a scanning cross-section that is observed when pressure is applied to the body tissue from the body surface with an ultrasound probe and the pressure is then released. In the second method, an acoustic radiation force or mechanical oscillations are applied from the body surface, shear waves then cause displacement of the body tissue, and the displacement is observed at each point along a scanning cross-section over time. This displacement is used to determine the propagation speed of the shear waves and the elasticity is then determined. In the former method, the local magnitude of distortion depends on the dynamic force due to an ultrasound probe being manually moved and an evaluation is made of whether an area of interest is hard or soft relative to the areas around the area of interest. On the other hand, in the latter method, the absolute elasticity of an area of interest can be determined.

In the latter method, a characteristic of shear waves is that they are reflected at the interfaces between tissues of different hardnesses. When displacement due to reflected shear waves is thus observed, the displacement can lead to inaccurate determination of the propagation speed of the shear wave and accordingly an artifact can occur in the hardness image displaying the hardness of body tissue. Consequently, various types of technologies have been proposed that will suppress these artifacts that are attributable to reflected shear waves.

BRIEF DESCRIPTION OF THE DRAWINGS

FIGS. 4A and 4B are flowcharts of a procedure taken by the ultrasound diagnosis apparatus according to the first embodiment;

FIG. 12 is a flowchart of a procedure taken by an ultrasound diagnosis apparatus according to a fourth embodiment.

DETAILED DESCRIPTION

An ultrasound diagnosis apparatus according to an embodiment includes a transmitter, a generator, and an output controller. The transmitter transmits push pulses that cause displacement in body tissue according to an acoustic radiation force from an ultrasound probe and transmits tracking pulses for measuring the displacement in the body tissue in a given scanning area, which is the displacement caused according to the push pulses, from the ultrasound probe. The generator generates transmission area image data displaying an transmission area to which the push pulses are transmitted. The output controller outputs the generated transmission area image data such that the generated transmission area image data is superimposed onto medical image data that contains the transmission area.

Ultrasound diagnosis apparatuses and imaging methods according to embodiments will be described with reference to the accompanying drawings.

First Embodiment

Figure 1:
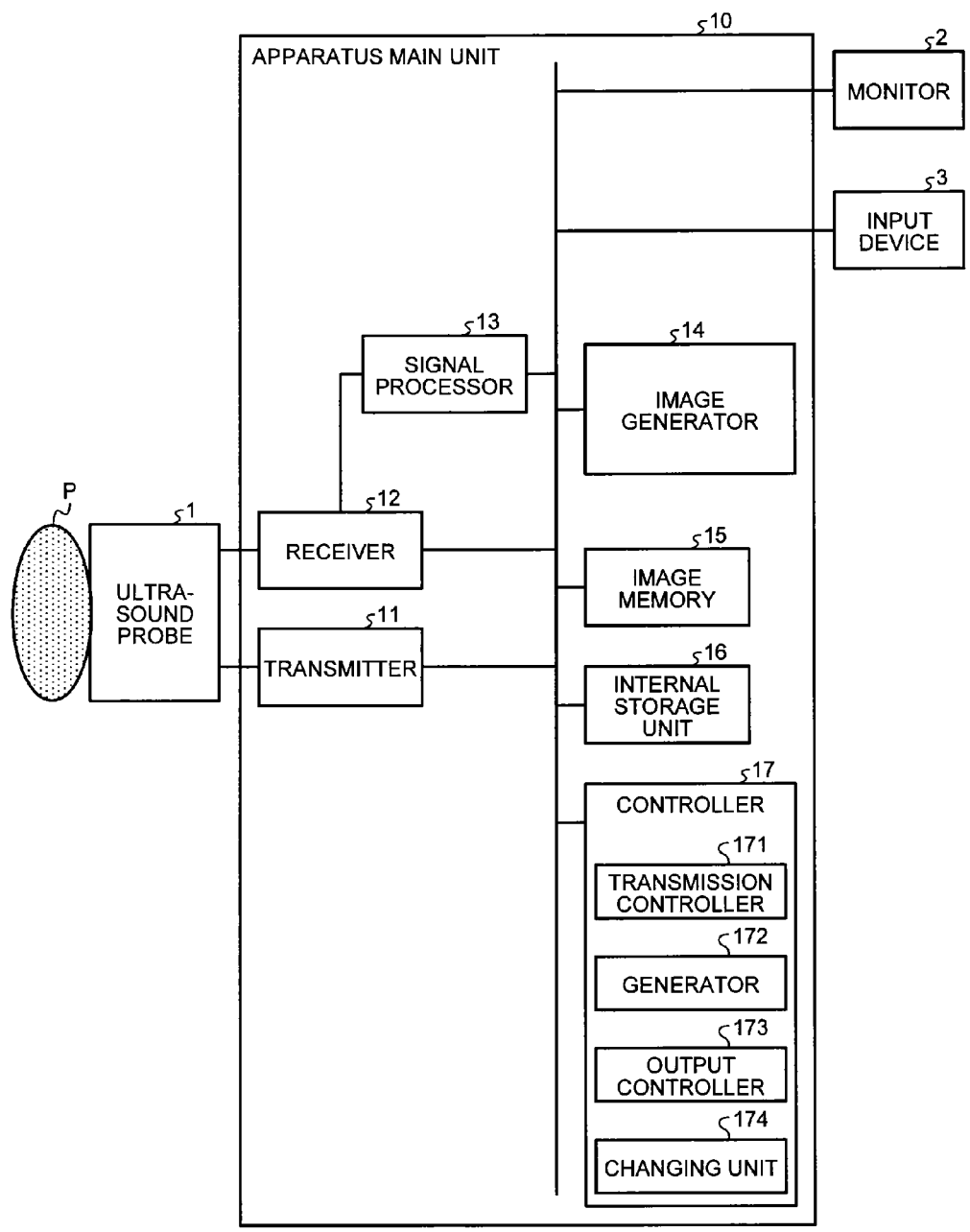
FIG. 1 is a block diagram of an exemplary configuration of an ultrasound diagnosis apparatus according to a first embodiment.

A configuration of an ultrasound diagnosis apparatus according to a first embodiment will be described first. FIG. 1 is a block diagram of an exemplary configuration of the ultrasound diagnosis apparatus according to the first embodiment. As illustrated in FIG. 1, the ultrasound diagnosis apparatus according to the first embodiment includes an ultrasound probe 1, a monitor 2, an input device 3, and an apparatus main unit 10.

The ultrasound probe 1 includes multiple oscillators (e.g. piezoelectric oscillators) that generate ultrasound according to a drive signal that is supplied from a transmitter 11 of the apparatus main unit 10, which will be described below. The multiple oscillators of the ultrasound probe 1 also receive reflected waves from a patient P and convert the reflected waves into electric signals. The ultrasound probe 1 includes a matching layer that is provided to the oscillators, a backing member that prevents backward ultrasound propagation from the oscillators.

When ultrasound is transmitted from the ultrasound probe 1 to the patient P, the transmitted ultrasound is sequentially reflected on a surface of tissue of the patient P where acoustic impedance discontinuity occurs and is received as reflected-wave signals by the multiple oscillators of the ultrasound probe 1. The amplitude of the received reflected-wave signals depends on the difference in acoustic impedance on the discontinuity surface on which ultrasound is reflected. The reflected-wave signals resulting from reflection of the transmitted ultrasound pulses on the flowing blood or the surface of, for example, the heart wall have a frequency shift due to the Doppler effects depending on the velocity components of the moving object in the direction in which ultrasound is transmitted.

In the first embodiment, the ultrasound probe 1 shown in FIG. 1 can be used in any of a case where the ultrasound probe 1 is a one-dimensional ultrasound probe in which multiple piezoelectric oscillators are arranged in a row, a case where the ultrasound probe 1 is a one-dimensional ultrasound probe in which multiple piezoelectric oscillators that are arranged in a row are caused to mechanically oscillate, and a case where the ultrasound probe 1 is a two-dimensional (2D) ultrasound probe in which multiple piezoelectric oscillators are arranged two-dimensionally in a matrix.

The input device 3 includes a mouse, a keyboard, a button, a panel switch, a touch command screen, a foot-switch, a trackball, a joystick, etc. The input device 3 receives various setting requests from an operator of the ultrasound diagnosis apparatus and transfers the received various setting requests to the apparatus main unit 10.

The monitor 2 displays a graphical user interface (GUI) for the operator of the ultrasound diagnosis apparatus to input various setting requests by using the input device 3 and displays ultrasound image data that is generated by the apparatus main unit 10, etc.

The apparatus main unit 10 is an apparatus that generates ultrasound image data on the basis of the reflected-wave signals that are received by the ultrasound probe 1. As shown in FIG. 1, the apparatus main unit 10 includes a receiver 12, a signal processor 13, an image generator 14, an image memory 15, an internal storage unit 16, and a controller 17.

The transmitter 11 controls directivity of transmission of ultrasound. Specifically, the transmitter 11 includes a rate pulser generator, a transmission delay unit, a transmission pulser and supplies a drive signal to the ultrasound probe 1. The rate pulser generator repeatedly generates rate pulses for forming ultrasound transmitted at a given rate frequency (pulse repetition frequency (PRF)). The rate pulses apply a voltage to the transmission pulser in a state where the rate pulses pass through the transmission delay unit and thus have different transmission delays. In other words, the transmitter delay unit gives, to each rate pulse generated by the rate pulser generator, a transmission delay for each oscillator necessary to focus the ultrasound generated by the ultrasound probe 1 into a beam and to determine the transmission directivity. The transmission pulser applies a drive signal (drive pulses) to the ultrasound probe 1 at a timing based on the rate pulses. The transmission direction or the transmission delay is stored in the internal storage unit 16, which will be described below, and the transmitter 11 refers to the internal storage unit 16 and controls the transmission directivity.

The drive pulses are transmitted to the oscillators in the ultrasound probe 1 via cables from the transmission pulser and then are converted from electric signals into mechanical oscillations. The mechanical oscillations are transmitted as ultrasounds in a living subject. The ultrasounds with different transmission delays of the respective oscillators converge and propagate in a given direction. By changing the transmission delay to be given to each rate pulse, the transmission delay unit arbitrarily adjusts the direction of transmission from the surface of the oscillator. The transmitter 11 gives transmission directivity by controlling the number and positions (transmission apertures) of the oscillators used to transmit ultrasound beams and the transmission delays corresponding to the positions of the respective oscillators constituting the transmission apertures. For example, the transmission delay circuit of the transmitter 11 gives a transmission delay to each rate pulse generated by the pulser circuit, thereby controlling the position of the point of convergence (transmission focus) in the depth direction of ultrasound transmission.

The transmitter 11 has a function of changing the transmission frequency, transmission drive voltage, etc. in order to implement a given scan sequence according to an instruction from the controller 17, which will be described below. Specifically, changing the transmission drive voltage is implemented by using a linear-amplifier transmitter circuit that can switch its value instantaneously or a mechanism for electrically switching between multiple power units.

The reflected waves of the ultrasound transmitted by the ultrasound probe 1 reach the oscillators in the ultrasound probe 1 and are then converted by the oscillators from the mechanical oscillations into electric signals (reflected-wave signals) and the electric signals are input to the receiver 12.

The receiver 12 controls the directivity of reception of ultrasound. Specifically, the receiver 12 includes a pre-amplifier, an A/D converter, a reception delay unit, and an adder and performs various types of processing on the reflected-wave signals that are received by the ultrasound probe 1 to generate reflected-wave data. The pre-amplifier amplifies the reflected-wave signals per channel to perform gain correction processing. The A/D converter performs A/D conversion on the gain-corrected reflected-wave signals and the reception delay unit gives a reception delay necessary to determine the reception directivity per channel. The adder sums the reflected-wave signals (digital signals) to which the reception delays are given and generates reflected-wave data. The summing by the adder enhances the reflection components from the direction corresponding to the directivity of reception of reflected-wave signals. The reception direction or reception delays are stored in the internal storage unit 16, which will be described below, and the receiver 12 refers to the internal storage unit 16 and controls the reception directivity. The receiver 12 according to the first embodiment is capable of parallel simultaneous reception.

The signal processor 13 performs various types of signal processing on the reflected-wave data generated from the reflected-wave signals by the receiver 12. The signal processor 13 performs logarithmic amplification, envelope detection processing, etc. on the reflected-wave data to generate data (B-mode image data) displaying the signal intensity at each sample point by luminance intensity.

The signal processor 13 also generates data (Doppler data) obtained by extracting the momentum information from the Doppler effects of the moving object at each sample point in the scanning area from the reflected-wave data received from the receiver 12. Specifically, the signal processor 13 generates Doppler data obtained by extracting the average velocity, variance, power value, etc. at each sample point as the momentum information on the moving object. The moving object is, for example, the blood flow, tissue of, for example, the heart wall, or a contrast agent.

The ultrasound diagnosis apparatus according to the first embodiment is an apparatus capable of performing elastography in which the distribution of measured hardnesses is visualized. Specifically, the ultrasound diagnosis apparatus according to the first embodiment is an apparatus capable of performing elastography by applying an acoustic radiation force and thus causing displacement of body tissue.

In other words, the transmitter 11 according to the first embodiment transmits, from the ultrasound probe 1, displacement-causing burst waves (push pulses) that cause displacement due to shear waves generated by an acoustic radiation force. The transmitter 11 according to the first embodiment transmits, from the ultrasound probe 1, observation pulses (tracking pulses) for observing the displacement caused by the displacement-causing burst waves for multiple times in each of multiple scanning lines of the scanning area. In other words, the transmitter 11 transmits, from the ultrasound probe, push pulses that cause displacement of body tissue according to the acoustic radiation force and transmits, from the ultrasound probe, tracking pulses for observing the displacement of body tissue in a given scanning area caused according to the push pulses. The observation pulses are transmitted in order to observe the propagation speed of the shear waves, which are generated by the displacement-causing burst waves, at each sample point in the scanning area. The observation pulse is normally transmitted in each scanning line of the scanning area for multiple times (e.g. for 100 times). The receiver 12 generates reflected-wave data from the reflected-wave signals of the observation pulses transmitted in each scanning line of the scanning area. The displacement-causing burst waves are an example of displacement-causing ultrasound. The observation pulses are an example of observation ultrasound.

The signal processor 13 analyzes the reflected-wave data of the observation pulse that is transmitted for multiple times in each scanning line of the scanning area and calculates hardness distribution information displaying the hardness distribution in the scanning area. Specifically, by measuring the propagation speed of the shear waves generated by the displacement-causing burst waves at each sample point, the signal processor 13 generates information on the hardness distribution in the scanning area.

For example, the signal processor 13 analyzes the frequency of the reflected-wave data of the observation pulses. Accordingly, the signal processor 13 generates momentum information (tissue Doppler data) over multiple time phases at multiple sample points in each scanning line. The signal processor 13 performs time integration on the speed components of the tissue Doppler data over multiple time phases that are acquired at each of the multiple sample points in each scanning line. In this manner, the signal processor 13 calculates the displacement at each of the multiple points in each scanning line over multiple time phases. The signal processor 13 then determines a time at which the maximum displacement is caused at each sample point. The signal processor 13 acquires the time at which the maximum displacement is caused at each sample point as the time at which the shear waves reach each sample point. The signal processor 13 then performs spatial differentiation on the time at which the shear waves reach each sample point to calculate the propagation speed of shear waves in each sample point. Hereinafter, a "propagation speed of shear waves" is referred to as a "shear wave speed" below.

The signal processor 13 generates hardness distribution information by color-coding the shear wave speed and mapping the color-coded shear wave speed at sample points. Hard tissue has a high shear wave speed and soft tissue has a low shear wave speed. In other words, the value of shear wave speed indicates the value of hardness (elastic modulus) of tissue. In the above-described case, observation pulses serve as tissue Doppler transmission pulses. The shear wave speed may be calculated by the signal processor 13 from the cross-correlation of displacement of tissue between adjacent scanning lines, not based on the time at which the maximum displacement is caused at each sample point.

The signal processor 13 may calculate a Young's modulus or a shear modulus from the shear wave speed and generate hardness distribution information from the calculated Young's modulus or shear modulus. Each of the shear wave speed, Young's modulus, and shear modulus can be used as a physical quantity that indicates the hardness of body tissue. A case will be described below where the signal processor 13 uses the shear wave speed as a physical quantity indicating the hardness of body tissue.

The shear waves that are generated by one transmission of displacement-causing burst waves propagate and attenuate. When observation of shear wave speed over a wide area is attempted, the shear waves that are generated due to the displacement-causing burst waves transmitted in a specific scanning line attenuate as they propagate and then cannot be observed at a sufficient distance from the position to which the displacement-causing burst waves are transmitted.

In such a case, it is required to transmit displacement-causing burst waves at multiple positions in the orientation direction. Specifically, the scanning area (or a region of interest) is divided into multiple areas along the orientation direction. Before transmission/reception observation pulses to/from each area (hereinafter, "divided area"), the transmitter 11 transmits displacement-causing burst waves at different scanning line positions so that shear waves are generated. Typically, the position to which displacement-causing burst waves are transmitted is set near each divided area. If the simultaneous parallel receptions are limited to a small number, the transmitter 11 performs processing for transmitting displacement-causing burst waves once and then transmitting observation pulses in each scanning line of a divided area for multiple times sequentially along the orientation direction in each of the multiple divided areas.

The image generator 14 generates ultrasound image data from the data generated by the signal processor 13. From the B-mode image data generated by the signal processor 13, the image generator 14 generates B-mode image data that displays the intensity of reflected waves by luminance. Furthermore, from the Doppler data generated by the signal processor 13, the image generator 14 generates Doppler image data that displays the moving object information. The Doppler image data is, for example, speed image data, distribution image data, power image data, or a combination thereof.

From the hardness distribution information generated by the signal processor 13, the image generator 14 generates hardness image data that displays the hardness of body tissue by colors. For example, the image generator 14 generates, as hardness image data, the shear wave speed image data obtained by plotting, in each point in the scanning area, a pixel value corresponding to the shear wave speed at each point in the scanning area.

The image generator 14 generally coverts the scanning line signals of ultrasound scanning into scanning line signals in a video format represented by a TV format etc. (i.e., performs scan conversion) and generate ultrasound image data to be displayed. Specifically, by performing coordinate conversion according to the mode of ultrasound scanning by the ultrasound probe 1, the image generator 14 generates the ultrasound image data to be displayed. Furthermore, in addition to scan conversion, the image generator 14 performs various types of image processing, such as image processing (smoothing processing) for reproducing a luminance-averaged image and image processing (edge enhancing processing) that uses a differential filter in an image, by using multiple image frames after scan conversion. The image generator 14 combines additional information (textual information of various parameters, scale mark, body mark, etc.) with the ultrasound image data.

In other words, the B-mode image data, Doppler data, and hardness distribution information are ultrasound image data prior to scanning conversion and the data generated by the image generator 14 is ultrasound image data posterior to scan conversion to be displayed. If the signal processor 13 generates three-dimensional (3D) data (3D B-mode image data, 3D Doppler data, and 3D hardness distribution information), the image generator 14 performs coordinate conversion according to the mode of ultrasound scanning by the ultrasound probe 1, thereby generating volume data. The image generator 14 then performs various types of rendering to generate 2D image data to be displayed.

The image memory 15 is a memory that stores image data to be displayed, which is generated by the image generator 14. The image memory 15 may store data that is generated by the signal processor 13. The B-mode image data, Doppler data, and hardness distribution information that are stored in the image memory 15 can be accessed by the operator, for example, after diagnosis and serve as ultrasound image data to be displayed via the image generator 14.

The internal storage unit 16 stores control programs for performing ultrasound transmission/reception, image processing, and display processing, diagnostic information (e.g. patient IDs and doctor's opinions), and various types of data such as diagnosis protocols and various body marks. The internal storage unit 16 is, as required, used to store the image data stored in the image memory 15. The data stored in the internal storage unit 16 can be transferred to an external device via an interface unit (not shown).

The internal storage unit 16 further stores information on the shear wave speed image data acquired by image capturing. For example, the internal storage unit 16 stores the time at which shear waves reach each sample point regarding the shear wave speed image data acquired by image capturing.

The controller 17 controls the whole processing performed by the ultrasound diagnosis apparatus. Specifically, according to various setting requests that are input by the operator via the input device 3 and various control programs and various types of data that are read from the internal storage unit 16, the controller 17 controls processing performed by the transmitter 11, the receiver 12, the signal processor 13, and the image generator 14. The controller 17 puts control such that the monitor 2 displays the ultrasound image data to be displayed, which is stored in the image memory 15.

The transmitter 11 and the receiver 12 incorporated in the apparatus main unit 10 may be configured by using processor hardware (CPU (Central Processing Unit), MPU (Micro Processing Unit), integrated circuit, etc.) or may be configured by using a program of a software module.

The general configuration of the ultrasound diagnosis apparatus according to the first embodiment has been described. The ultrasound diagnosis apparatus according to the first embodiment having the above-described configuration transmits displacement-causing burst waves and visualizes the hardness of body tissue.

In this method, generally, after shear waves are generated, changes in displacement near each point (sample point) are observed over time and the time at which the peak of displacement is caused is determined as the time at which the shear waves reach. By obtaining a spatial differential of the time at which the shear waves reach, a local shear wave speed can be determined. However, it is known that the time at which shear waves reach is not necessarily calculated properly because generated shear waves are reflected at the interfaces (structure boundary) between tissues of different hardnesses and this results in time-displacement curves different from expected ones, and thus an artifact can occur in a hardness image (shear wave speed image or elasticity image) that is displayed eventually.

Figure 2A:
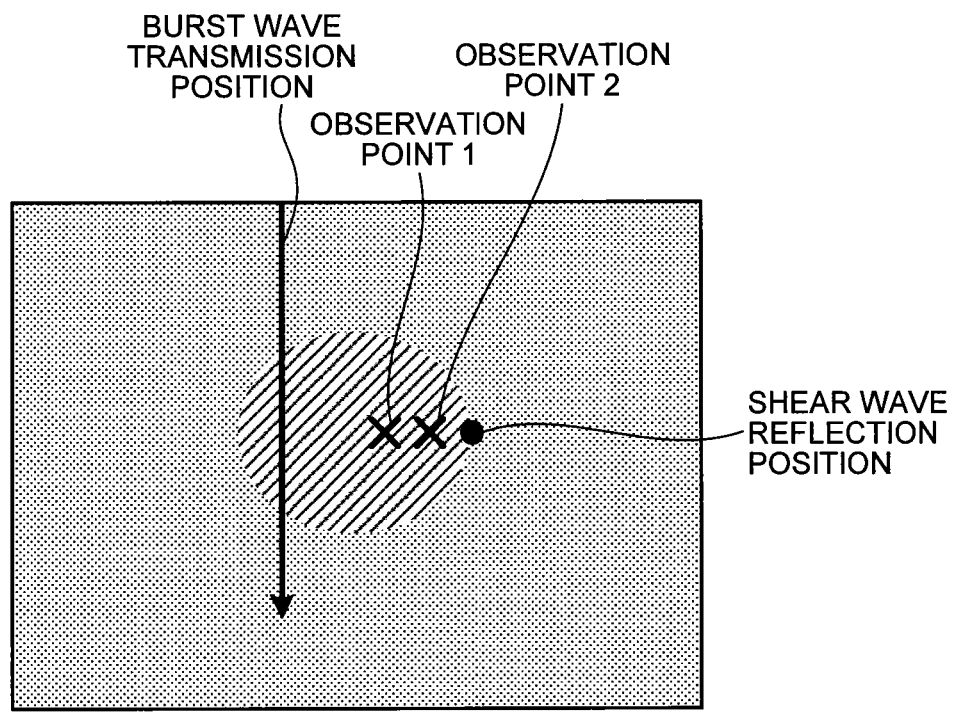
FIGS. 2A to 3B illustrate a problem.
Figure 2B:
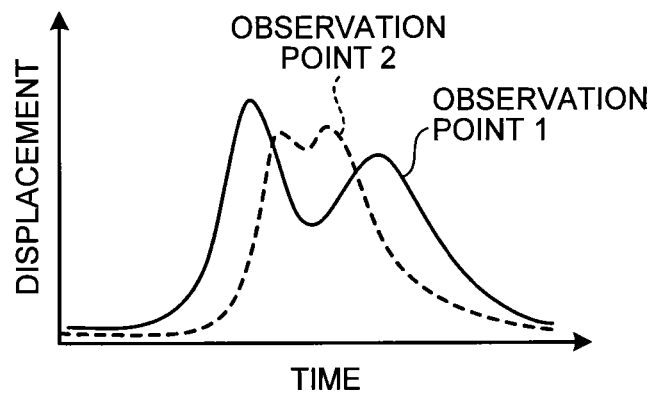
Figure 2C:
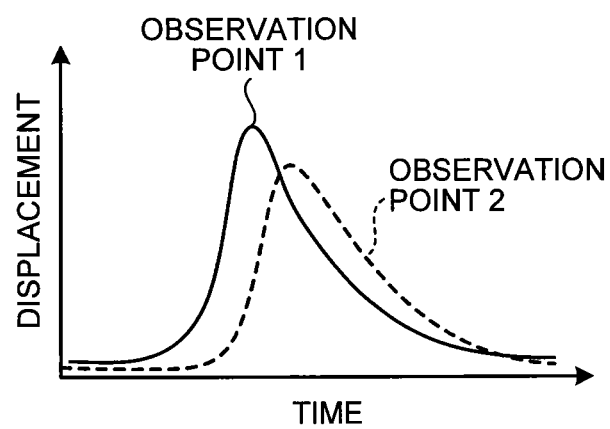

FIGS. 2A to 2C illustrate a problem. FIG. 2A shows an exemplary B-mode image. The hatched oval area positioned at the center of the image represents tissue whose hardness is different from those of other areas. In other words, the outline of the hatched area corresponds to a structure boundary. Furthermore, a burst wave transmission position represents the position to which displacement-causing burst waves are transmitted and an observation point corresponds to a sample point at which displacement that is caused due to displacement-causing burst waves is observed. FIG. 2B shows exemplary time-displacement curves containing reflected components and FIG. 2C shows exemplary time-displacement curves obtained by excluding the reflected components from the curves shown in FIG. 2B. The horizontal axis and vertical axis shown in FIGS. 2B and 2C indicate the time and magnitude of displacement, respectively.

As shown in FIG. 2A, when displacement-causing burst waves are transmitted, shear waves propagate from the burst wave transmission position. The shear waves that propagate rightward from the burst wave transmission position in FIG. 2 are observed at Observation point 1 and then at Observation point 2. The shear waves that further propagate are reflected at the shear wave reflected position shown in FIG. 2A and then propagate leftward. The shear waves that are reflected and propagate are observed at Observation point 1 and then at Observation point 2. The time-displacement curves at Observation point 1 and Observation point 2 are shown in FIG. 2B.

As shown in FIG. 2B, the displacement due to shear waves that propagate directly (without being reflected) from the burst wave transmission position is at peak at Observation point 1 at first and then is at peak at Observation point 2. Thereafter, the displacement due to the shear waves that are reflected at the shear wave reflection position is at peak at Observation point 2 and is then at peak at Observation point 1. For example, the time at which shear waves reach is observed as the time at which displacement of the shear waves that directly propagate from the burst wave transmission position is at peak. As shown in FIG. 2B, when the time-displacement curve contains the peak of displacement due to the reflected shear waves, for example, the peak time is erroneously observed and thus an artifact occurs in the shear wave speed image.

For example, has been proposed a technology for suppressing artifacts that are attributable to reflection of shear waves by excluding the components of shear waves propagating in a given direction by using the spatial distribution of time-displacement curves. According to this technology, the time-displacement curves shown in FIG. 2C are acquired by excluding the components of the reflected shear waves from the time-displacement curves (reflected components) shown in FIG. 2B and this prevents erroneous observation of reflected components. However, this method cannot exclude the effects of the reflected shear waves propagating in the same direction. This aspect will be described below with reference to FIGS. 3A and 3B.

Figure 3A:
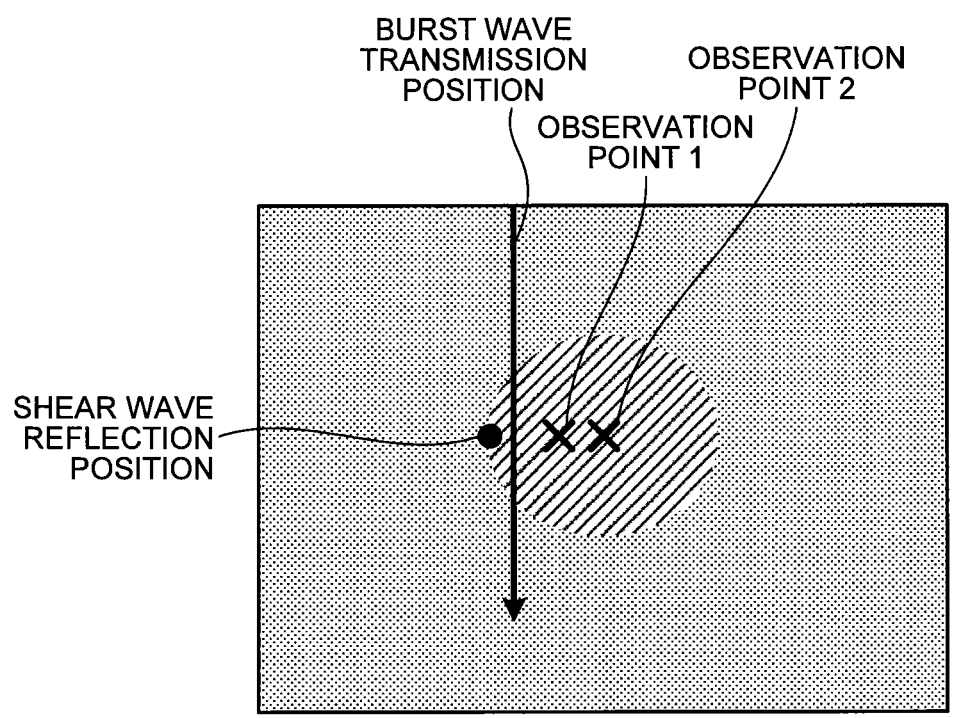
Figure 3B:
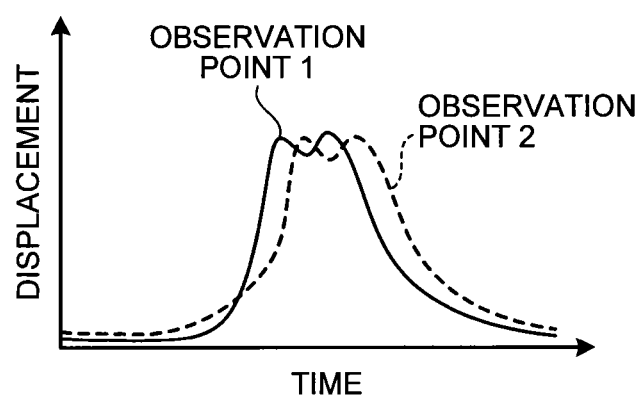

FIGS. 3A and 3B illustrate the problem. FIG. 3A is an exemplary B-mode image. As shown in FIG. 3A, the oval hatched area positioned at the center of the image represents tissue whose hardness is different from those of other areas and, compared to FIG. 2A, the burst wave transmission position and the shear wave reflection position are close to each other. FIG. 3B represents exemplary time-displacement curves containing reflected components. The horizontal axis and vertical axis shown in FIG. 3B indicate the time and magnitude of displacement, respectively.

As shown in FIG. 3A, when displacement-causing burst waves are transmitted, shear waves propagate from the burst wave transmission position. The shear waves that propagate rightward from the burst wave transmission position in FIG. 3A propagate from the burst wave transmission position directly to Observation point 1 and Observation point 2. On the other hand, shear waves that propagate leftward from the burst wave transmission position are reflected at a near shear wave reflection position and then propagate to Observation point 1 and Observation point 2. In this manner, when displacement-causing burst waves are transmitted at a position near the interface, is observed displacement in which shear waves that propagate from the position where the shear waves are generated directly to the observation points are followed by shear waves that are reflected at the interface and then propagate. In this case, because the directly-propagating shear waves and the shear waves that are reflected and then propagate propagate in the same direction, the reflected components cannot be excluded by using the above-described method.

Furthermore, in general, displacement of tissue that is caused due to displacement-causing burst waves is minute and thus is susceptible to various noises. For example, when the time at which the displacement is at maximum as shown in FIG. 3B is detected as a reach time, the earlier one of the two peaks, i.e., the reach time corresponding to the shear waves that directly propagate, should be detected. However, if there is an external cause, such as body motion or hand jiggling, the latter peak has greater amplitude so that the latter peak time is detected as the time at which shear waves reach. If an error occurs in detection of a reach time, the error may appear as a significant artifact when a shear wave speed is calculated by performing a spatial differential on the time at which shear waves reach. In order to solve such a problem, when multiple peaks are found, may be contrived a reach time detection method in which, for example, the first peak is detected as a reach time or a general time difference is detected on the basis of the cross-correlation, not by detecting a maximum value, to determine a reach time. However, such methods are susceptible to disturbance (variation in the time-displacement curves due to power noise or motion of the body) resulting from a cause other than reflected shear waves and there is a possibility that the reach time cannot be detected robustly. Furthermore, the latter method increases the calculation costs and thus lowers the real-time property.

The above-described problem tends to occur when there is a structure boundary near a position to which displacement-causing burst waves are transmitted. The structure boundary may be confirmed sufficiently in a B-mode image. In such a case, it is assumed that, if the operator can avoid inclusion of a structure boundary near a position at which displacement-causing burst waves are transmitted (transmission area), artifacts due to reflected components can be suppressed. However, in a conventional ultrasound diagnosis apparatus, displacement-causing burst waves are generally transmitted to multiple spots in a shear wave speed image area but at which positions displacement-causing burst waves are transmitted is not represented to the operator. For this reason, the operator cannot know to which parts displacement-causing burst waves are transmitted and, even when the operator understands that artifacts typically occur as described above, the operator cannot positively avoid such a situation.

For this reason, the ultrasound diagnosis apparatus according to the first embodiment includes a display unit that clearly displays positions at which displacement-causing burst waves are transmitted before or while a shear wave speed image is acquired. For example, when a region of interest (ROI) for displaying a shear wave speed image is set in the B-mode image, multiple positions at which displacement-causing burst waves are transmitted are displayed simultaneously. Furthermore, for example, when at least one of the positions at which displacement-causing burst waves are transmitted is near the interface between tissues of different hardnesses, the position to which displacement-causing burst waves are transmitted can be changed or the number of positions at which displacement-causing burst waves are transmitted can be changed.

The following descriptions refer back to FIG. 1. In the ultrasound diagnosis apparatus according to the first embodiment, the controller 17 includes a transmission controller 171, a generator 172, an output controller 173, and a changing unit 174.

The transmission controller 171 controls transmission of displacement-causing burst waves and transmission/reception of observation pulses performed by the transmitter 11. For example, the transmission controller 171 receives an instruction for determining an ROI from the operator. According to the received instruction, the transmission controller 171 sets positions at which displacement-causing burst waves are transmitted, the number of transmission positions, the position of ROI, the area (size) of ROI, the number of ROIs, etc. for generating shear wave speed image data corresponding to the ROI. Under the control of the transmission controller 171, the transmitter 11 transmits displacement-causing burst waves from the ultrasound probe 1. Under the control of the transmission controller 171, the transmitter 11 further transmits, for multiple times, observation pulses for observing displacement that is caused due to the transmitted displacement-causing burst waves from the ultrasound probe 1 in each of multiple scanning lines of the scanning area.

The generator 172 generates transmission position image data displaying burst wave transmission positions (push pulse lines) and a scanning area image data displaying the position of the scanning area. For example, the generator 172 acquires the burst wave transmission position that is set by the transmission controller 171. The generator 172 then generates linear image data (indicator) indicating the acquired burst wave transmission position as transmission position image data. Furthermore, the generator 172 acquires the position and size of ROI that are set by the transmission controller 171. The generator 172 then generates, as scanning area image data, rectangular-frame image data displaying the acquired position and size of ROI.

The output controller 173 outputs the generated transmission position image data and scanning area image data such that the generated transmission position image data and scanning area image data are superimposed onto the ultrasound image data. For example, the output controller 173 displays transmission position image data and scanning area image data, which are generated by the generator 172, such that the transmission position image data and scanning area image data are superimposed onto a B-mode image.

The changing unit 174 receives change instructions for changing the position to which displacement-causing burst waves are transmitted, the number of transmission positions, the position of scanning area, the area of scanning area, or the number of scanning areas. According to the received change instructions, the changing unit 174 changes the position at which the transmitter 11 transmits displacement-causing burst waves, the number of transmission positions, the position of scanning area, the area of scanning area, or the number of scanning areas.

Figure 4B:
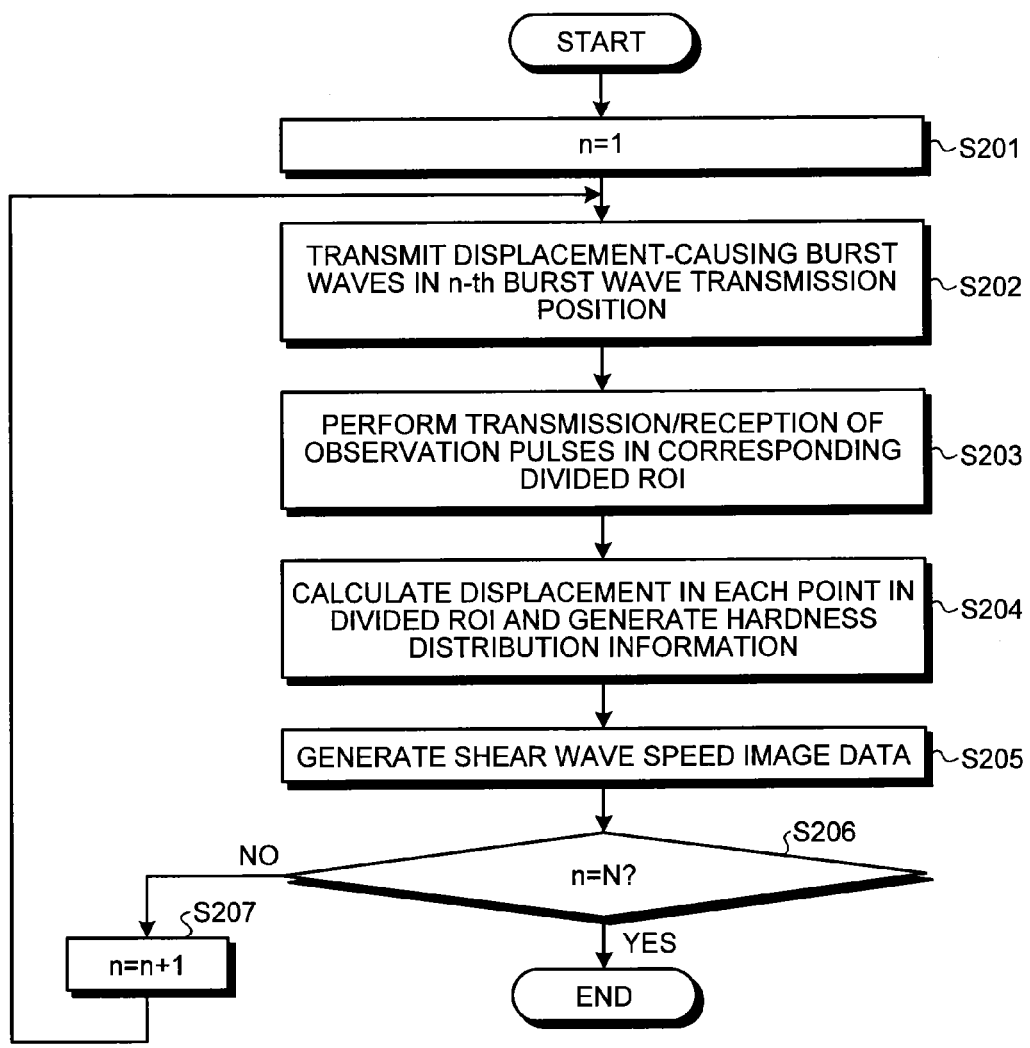

FIGS. 4A and 4B are flowcharts of a procedure taken by the ultrasound diagnosis apparatus according to the first embodiment. With reference to FIGS. 5A to 5D, the procedure taken by the ultrasound diagnosis apparatus according to the first embodiment will be described. FIGS. 5A to 5D illustrate the processing performed by the ultrasound diagnosis apparatus according to the first embodiment.

As shown in FIG. 4A, the transmission controller 171 of the ultrasound diagnosis apparatus according to the first embodiment determines whether a start instruction for starting a hardness image generation mode for generating a hardness image is received from an operator (step S101). The hardness image generation mode is, for example, a state where an ROI for generating a hardness image is set and, after the ROI is set, displacement-causing burst waves are transmitted and thus a hardness image is generated. When a start instruction is not received (NO at step S101), the controller 17 waits until a start instruction is received.

Figure 5A:
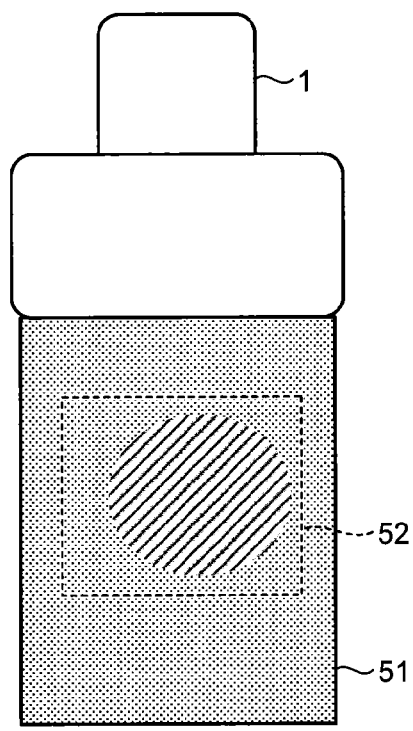
FIGS. 5A to 5D illustrate processing performed by the ultrasound diagnosis apparatus according to the first embodiment.

On the other hand, when a start instruction is received (YES at step S101), the monitor 2 displays an ROI setting GUI under the control of the transmission controller 171 (step S102). The ROI setting GUI that is displayed on the monitor 2 will be described here with reference to FIG. 5A. As shown in FIG. 5A, for example, a B-mode image 51 that is obtained by scanning with the ultrasound probe 1 is displayed on the monitor 2. The monitor 2 displays, on the B-mode image 51, an ROI 52 that specifies an area in which a shear wave speed image is generated. The size and position of the ROI 52 is pre-set. The transmission controller 171 receives instructions for changing the size and position of the ROI 52 from the operator and changes the size and position of the ROI 52 according to the received instructions.

The transmission controller 171 determines whether the ROI 52 is determined (step S103). For example, the transmission controller 171 determines whether the ROI 52 is determined according to whether an instruction for determining the ROI 52 is received from the operator. When an ROI is not determined (NO at step S103), the transmission controller 171 waits until an ROI is set. On the other hand, when the ROI 52 is determined (YES at step S103), the transmission controller 171 divides the determined ROI 52 into divided ROIs (step S104) and calculates burst wave transmission positions corresponding to the ROIs, respectively (step S105).

The reason for diving the ROI 52 into divided ROIs will be described here. In elastography, for example, displacement-causing burst waves are transmitted at an end of the ROI 52, propagation of the shear waves thus generated to the other end of the ROI 52 is observed, and the speed of propagation is displayed by an image. In this case, because displacement caused by the displacement-causing burst waves is generally minute in few to few tens of micrometers and furthermore the shear waves from the displacement attenuate while propagating, only few millimeters of shear waves can be observed. For this reason, in order to acquire a shear wave speed image of a relatively wide area, displacement-causing burst waves are transmitted to multiple spots, a shear wave speed image of few millimeters of shear wave propagation occurring in each of the spots is generated, and the multiple shear wave speed images are combined when displayed eventually. Thus, when the ROI 52 is determined, the transmission controller 171 divides the ROI 52 into small areas (divided ROIs) according to the size of the specified ROI 52. The transmission controller 171 then determines positions at which displacement-causing burst waves are transmitted that correspond to the respective small areas.

The processing at steps S104 and S105 will be described below. For example, the transmission controller 171 calculates a required number of divided ROIs on the basis of the lateral width of the ROI 52, which is determined at step S103, and the upper limit value of the width of ROI. The upper limit value of the ROI width is, for example, previously stored in the internal storage unit 16. For example, if the width of the ROI 52 that is set as shown in FIG. 5A is 2.7 cm and the upper limit value of the ROI width is 1.0 cm, three ROIs each having a width of 0.9 cm (divided ROIs 53, 54 and 55) are set. Alternatively, for example, two divided ROIs each having a width of 1.0 cm and a divided ROI having a width of 0.7 cm may be set.

The transmission controller 171 then determines a position to which displacement-causing burst waves are transmitted for observing the shear wave speed in each divided ROI. Because, in general, the shear wave speed cannot be determined properly at a position where displacement is caused, it is preferable that displacement-causing burst waves be transmitted to the outside of the area about which a shear wave speed image is acquired. For example, an offset value that defines the distance between a burst wave transmission position and a divided ROI is stored in the internal storage unit 16. The transmission controller 171 calculates a position that is distant, by the offset value, from the left end of each of set divided ROIs as a burst wave transmission position. In the example shown in FIG. 5B, the transmission controller 171 calculates burst wave transmission positions 56, 57, and 58 as transmission positions for observing a shear wave speed in the respective divided ROIs 53, 54, and 55.

As described above, the transmission controller 171 divides the ROI 52 into the divided ROIs 53, 54, and 55 and calculates the burst wave transmission positions 56, 57, and 58 corresponding to the divided ROIs 53, 54, and 55, respectively. For the embodiment, the case has been described where the ROI 52 is divided and the divided ROIs 53, 54, and 55 are set. Alternatively, for example, it is not necessary to divide the ROI 52 if the width of the determined ROI 52 is smaller than the upper limit value.

Figure 5B:
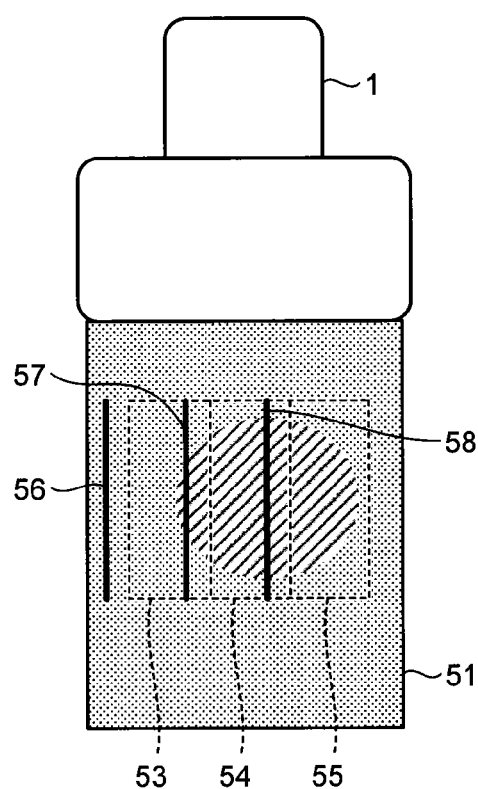

The generator 172 then generates transmission position image data and divided ROI image data (step S106). For example, as shown in FIG. 5B, the generator 172 acquires the burst wave transmission positions that are set by the transmission controller 171. The burst wave transmission positions represent transmission areas to which push pulses are transmitted from the ultrasound probe 1 and are also referred to as push pulse lines. The generator 172 then generates transmission position image data (transmission area image data) displaying the acquired burst wave transmission positions. The generator 172 then acquires the position and size of ROI that is set by the transmission controller 171. The ROI includes small areas (divided ROIs) corresponding to the burst wave transmission positions. The generator 172 then generates scanning area image data displaying the acquired position and size of ROI.

FIG. 5B illustrates the case where the burst wave transmission positions are displayed by linearly image data. Alternatively, for example, a burst wave transmission position may be displayed by an arrow image data indicating, in addition to the position to which push pulses are transmitted, the direction of the transmission. Alternatively, a burst wave transmission position may be displayed by data of an image in a shape that narrows toward the focus position and expand rearward with respect to the focus position (a shape with a narrow part).

The output controller 173 displays the transmission position image data and divided ROI image data such that the transmission position image data and divided ROI image data are superimposed onto the B-mode image data (step S107). For example, as shown in FIG. 5B, the output controller 173 acquires, from the generator 172, the transmission position image data displaying each of the burst wave transmission positions 56, 57, and 58 and the divided ROI image data displaying each of the divided ROIs 53, 54, and 55, which are generated by the generator 172 as shown in FIG. 5B. The output controller 173 then superimposes the acquired transmission position image data displaying each of the burst wave transmission positions 56, 57, and 58 and the divided ROI image data displaying each of the divided ROIs 53, 54, and 55 onto the B-mode image data and displays the superimposed data on the monitor 2.

According to change instructions from the operator, the changing unit 174 then changes the burst wave transmission position and the divided ROI (step S108). When the changing unit 174 receives no change instruction, the processing at step S110 may be performed, without performing the processing at steps S108 and S109.

Figure 5C:
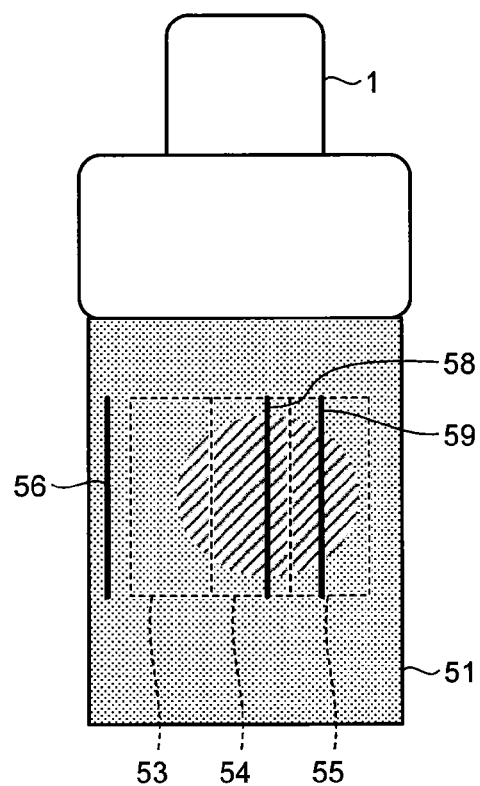
Figure 5D:
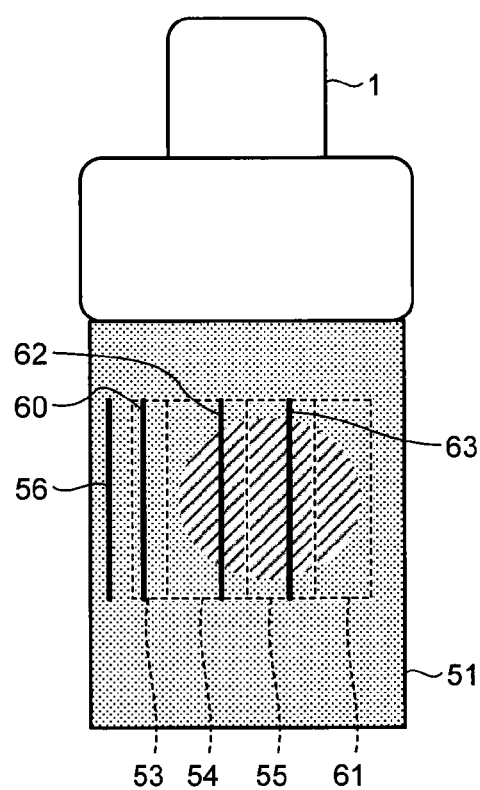

The processing performed by the changing unit 174 will be describe with reference to FIGS. 5B to 5D. A case will be described here where the display image shown in FIG. 5B is displayed by the processing before step S107.

The operator recognizes that the burst wave transmission position 57 corresponding to the divided ROI 54 from among the three divided ROIs 43, 54, and 55 is close to the oval structure boundary. The operator selects the burst wave transmission position 57 here by using the input device 3 and gives an instruction for changing the burst wave transmission position 57. For example, the operator makes an adjustment to shift the burst wave transmission position 57 toward or distant from the left end of the divided ROI 54. In another example, the changing unit 174 may be configured to select a position distant from the left end of the divided ROI 54 by the offset value or a position distant from the right end of the divided ROI 54 by the offset value such that the operator selects any one of the positions. In other words, the changing unit 174 may set a limit on the positions that the operator can select. This is because if, for example, a burst wave transmission position is set at a position away from a divided ROI by a certain distance or more, the shear waves generated at the position attenuate completely before reaching the target divided ROI and displacement sufficient to determine the shear wave speed in the target divided ROI cannot be obtained. On the other hand, if a burst wave transmission position is set at a position close to a target divided ROI with a certain distance or less or is set in the target ROI, the shear wave speed cannot be determined properly near that position. Alternatively, the operator may arbitrarily set a burst wave transmission position to some extent and the size of a small area and the number of small areas may be automatically changed according to the set position.

For example, as shown in FIG. 5C, the changing unit 174 receives a change instruction for changing the burst wave transmission position 57 to a burst wave transmission position 59 from the operator. According to the received change instruction, the changing unit 174 changes the burst wave transmission position 57 to the burst wave transmission position 59.

For example, as shown in FIG. 5D, upon receiving a change instruction for changing the burst wave transmission position 57 to a burst wave transmission position 60 from the operator, the changing unit 174 automatically changes the position and size of divided ROI and the number of divided ROIs in accordance with the burst wave transmission position 60 to which the burst wave transmission position 57 is changed. Specifically, when the burst wave transmission position 57 is changed to the burst wave transmission position 60, the changing unit 174 shifts leftward the position of the left end of the divided ROI 54 corresponding to the burst wave transmission position 57 such that the distance between the left end of the divided ROI 54 and the burst wave transmission position 60 is equal to the offset value. The changing unit 174 then shifts leftward the position of the right end of the divided ROI 54 such the width of the divided ROI 54 is within the upper limit value of the ROI width. Accordingly, the width of the divided ROI 55 exceeds the upper limit value of the ROI width. For this reason, the changing unit 174 further divides the divided ROI 55. In the example shown in FIG. 5D, the right area of the divided ROI 55 is allocated as another divided ROI 61 and accordingly the widths of all divided ROIs can be equal to or less than the upper limit value of the ROI width. In accordance with the change of the position of the left end of the divided ROI 55 (the right end of the divided ROI 54), the changing unit 174 also shifts the burst wave transmission position 58 leftward by a distance equal to the distance by which the left end of the divided ROI 55 is shifted (leading to a burst wave transmission position 62). The changing unit 174 further determines a burst wave transmission position 63 corresponding to the divided ROI 61 and generates and displays transmission position image data in the determined position.

For the example shown in FIG. 5D, the case has been described where, in accordance with the burst wave transmission position to which a burst wave transmission position is changed, various parameters, such as other burst wave transmission positions, the number of burst wave transmission positions, the position of divided ROI, the area of divided ROI, or the number of divided ROIs, are automatically changed. Alternatively, in response to a change in any one of the parameters, the changing unit 174 may automatically change other parameters on the basis of the offset value and ROI width upper limit value. Accordingly, the operator can easily change various parameters and furthermore can prevent the changed parameters from deviating from the offset value or ROI width upper limit value. Furthermore, the changing unit 174 may change all parameters according to the operator's discretion. In other words, the changing unit 174 receives change instructions for changing various parameters and, according to the received change instructions, changes the parameters. In this case, because the operator can change all parameters to arbitrary values the operator's discretion can be reflected to details. Furthermore, for example, when there is no significant structure in an ROI and it can be assumed that reflection or refraction of shear waves will not occur, by increasing the number of positions in which displacement-causing burst waves are transmitted, shear wave propagation can be observed only in an area where sufficient displacement is caused and consequently the image quality can be improved.

In the example shown in FIG. 5B, it is not necessary to change the burst wave transmission position 58 because the structure boundary near the burst wave transmission position 58 is almost perpendicular to the burst wave transmission position 58 and there is a low risk that reflected shear waves that propagate in the same direction as that of shear waves are caused.

As described above, the changing unit 174 receives change requests for changing various parameters, such as the position to which displacement-causing burst waves are transmitted, the number of transmission positions, the position of scanning area, the area of scanning area, or the number of scanning areas. According to the received change instructions, the changing unit 174 then changes various parameters.

The following descriptions refer back to FIG. 4A. The output controller 173 displays the post-change transmission position image data and divided ROI image data such that the post-change transmission position image data and divided ROI image are superimposed onto the B-mode image data (step S109). For example, when the changing unit 174 shifts the burst wave transmission position, the output controller 173 shifts the transmission position image data corresponding to the shifted burst wave transmission position and displays the transmission position image data on the monitor 2. Furthermore, for example, when the changing unit 174 adds a divided ROI, the changing unit 174 causes the generator 172 to generate divided ROI image data corresponding to the added divided ROI and displays the generated divided ROI image data on the monitor 2.

By performing the above-described processing, N sets of transmission position image data and N sets of divided ROI image data are displayed on the B-mode image 51. In other words, the transmission controller 171 sets N separated positions to which burst waves are transmitted in order to scan the whole area of the ROI 52 and N divided ROIs for observing shear waves generated by the transmitted burst waves.

The transmission controller 171 determines whether a request for starting image capturing to acquire shear wave speed image data is received from the operator (step S110). When no image capturing start request is received (NO at step S110), the transmission controller 171 waits until an image capturing start request is received.

In contrast, when an image capturing start request is received (YES at step S110), the transmission controller 171 performs processing for generating shear wave speed image data (step S111). The processing for generating shear wave speed image data will be described here with reference to FIG. 4B.

As shown in FIG. 4B, the transmission controller 171 makes a setting of "n=1" (step S201). Under the control of the transmission controller 171, the transmitter 11 transmits displacement-causing burst waves from the ultrasound probe 1 at an n-th burst wave transmission position (step S202). Under the control of the transmitter 11 and the receiver 12, the ultrasound probe 1 transmits/receives observation pulses in a divided ROI corresponding to the displacement-causing burst waves (step S203). For example, observation pulses are transmitted/received to/from a scanning line (raster) in the divided ROI for multiple times (about 100 times). Accordingly, changes in displacement over time at each point (each sample point) are calculated. If a system that can perform multiple receptions corresponding to a single pulse is used, changes in displacement over time over the area of the ROI can be known from one transmission of displacement-causing burst waves. However, if the number of simultaneous receptions is limited, multiple transmissions/receptions of observation pulses are performed for multiple times in different raster positions. In that case, each time when observation pulses are transmitted in a different raster position, displacement-causing burst waves are transmitted.

The signal processor 13 then calculates the displacement at each point (each sample point) of the divided ROI and generates hardness distribution information (step S204). To calculate the displacement, a method of calculating a Doppler shift between two echo signals, a method of calculating a cross-correlation, etc. can be used. On the basis of the changes in displacement over time at each point, the signal processor 13 calculates the time at which shear waves reach each point and calculates the shear wave speed at each point.

The image generator 14 then generates shear wave speed image data corresponding to the n-th burst wave transmission position (step S205). The transmission controller 171 then determines whether "n=N" is satisfied (step S206). When "n=N" is not satisfied (NO at step S206), the transmission controller 171 increments "n" to satisfy "n=n+1" (step S207) and the transmitter 11 returns to step S202 and transmits displacement-causing burst waves from the ultrasound probe 1 at the n-th burst wave transmission position.

On the other hand, when "n=N" is satisfied (YES at step S206), the transmission controller 171 ends the process for generating shear wave speed image data. The above-described processing generates N sets of shear wave speed image data.

The following descriptions refer back to FIG. 4A. According to an instruction from the transmission controller 171, the image generator 14 combines the N sets of shear wave speed image data to generate composite image data (step S112). Under the control of the transmission controller 171, the monitor 2 displays the composite image data that is the shear wave speed image data on the whole ROI (step S113). The image capturing processing for acquiring shear wave speed image data ends here.

If the request that is input by the operator is request for image capturing to acquire a video image of shear wave speed image data, the processing from step S111 to step S113 is repeated under the control of the transmission controller 171 until image capturing end request is received.

For the above-described procedure, the case has been described where the burst wave transmission position or the divided ROI is changed before receiving a request for starting image capturing to acquire shear wave speed image data from the operator. However, embodiments are not limited to this. For example, the burst wave transmission position or the divided ROI may be changed after the shear wave speed image data is acquired by mage capturing. In this case, the operator can change the burst wave transmission position while viewing the shear wave speed image that is update in realtime.

As described above, the ultrasound diagnosis apparatus according to the first embodiment generates transmission position image data and scanning area image data and displays the generated transmission position image data and scanning area image data such that the transmission position image data and scanning area image data are superimposed onto B-mode image data. Accordingly, the operator can confirm by sight the burst wave transmission positions and scanning area. Thus, for example, by confirming the position of a structure boundary where shear waves are likely to be reflected while comparing the B-mode image and the burst wave transmission positions and by handling the ultrasound probe 1 to change the position or direction of the ultrasound probe 1, the user can avoid the situation where an artifact is likely to occur due to reflection of shear waves. In other words, the operator can avoid that the structure boundary is included near the position to which displacement-causing burst waves are transmitted. Consequently, the ultrasound diagnosis apparatus according to the first embodiment can improve the image quality of the hardness image.

Furthermore, for example, the ultrasound diagnosis apparatus according to the first embodiment receives change instructions for changing various parameters, such as the position to which displacement-causing burst waves are transmitted, the number of transmission positions, the position of scanning area, the area of scanning area, or the number of scanning areas. According to the received change instructions, the ultrasound diagnosis apparatus changes various parameters. Accordingly, the operator can avoid a situation where an artifact is likely to occur due to reflection of shear waves even when it is difficult to avoid interfaces between tissues of different hardnesses only by changing the position and direction of the ultrasound probe 1.

Furthermore, according to the operator's discretion, the operator can avoid positions in which transmission of displacement-causing burst waves having a great acoustic energy should be avoided, such as the vicinity of a highly-reflective object, e.g. bone, and plaque or tumor that may rupture.

Furthermore, selection of a burst wave transmission position according to the operator's discretion allows the operator to easily investigate and know the connection between the structural characteristic in the vicinity of the burst wave transmission position and an artifact to occur, which eventually allows the operator to positively improve the image quality of the shear wave speed image. On the other hand, when no significant structure is found in the ROI, the image quality can be further improved by increasing the number of burst wave transmission positions.

For the first embodiment, the case has been described where the changing unit 174 changes various parameters according to change instructions from the operator. However, embodiments are not limited to this. For example, the ultrasound diagnosis apparatus does not necessarily include the changing unit 174. In this case, the operations and the apparatus configuration can be simplified. Even in this case, the ultrasound diagnosis apparatus generates and displays transmission position image data and scanning area image data, which allows the operator to confirm by sight burst wave transmission positions and scanning area. Consequently, by changing the position or direction of the ultrasound probe, the operator can avoid a situation where an artifact is likely to occur due to reflection of shear waves.

For the first embodiment, the case has been describe where the ultrasound diagnosis apparatus generates and displays transmission position image data and scanning area image data. However, embodiments are not limited to this. For example, the ultrasound diagnosis apparatus may generate and display only any one of transmission position image data and scanning area image data. In this case, by keeping transmission position image data or scanning area image data sufficiently apart from a structure boundary displayed on the monitor 2, the operator can avoid a situation where an artifact is likely to occur due to reflection of shear waves.

Display and non-display of burst wave transmission positions and divided ROIs may be switched according to an instruction from the user. For example, at step S113 in FIG. 4A, when composite image data of shear wave speed image data is displayed, the output controller 173 does not display the burst wave transmission positions and divided ROIs. When the composite image data is not displayed and the B-mode image is displayed, the output controller 173 re-displays the burst wave transmission positions and divided ROIs.

For the first embodiment, the case has been described where an ROI is divided horizontally (laterally). Alternatively, an ROI may be divided horizontally (in the depth direction).

Second Embodiment

For the first embodiment, the case has been described where the operator confirms by sight and determines whether there is a structure boundary that is likely to reflect shear waves near a burst wave transmission position. However, embodiments are not limited to this. For example, the ultrasound diagnosis apparatus may determine whether there is a structure boundary near a burst wave transmission position. Thus, for a second embodiment, a case will be described where an ultrasound diagnosis apparatus determines whether there is a structure boundary near a burst wave transmission position and, according to the determination result, calls the operator's attention by using a display or outputting a warning sound or a burst wave transmission position is re-set at a position sufficiently away from the structure boundary.

Figure 6:
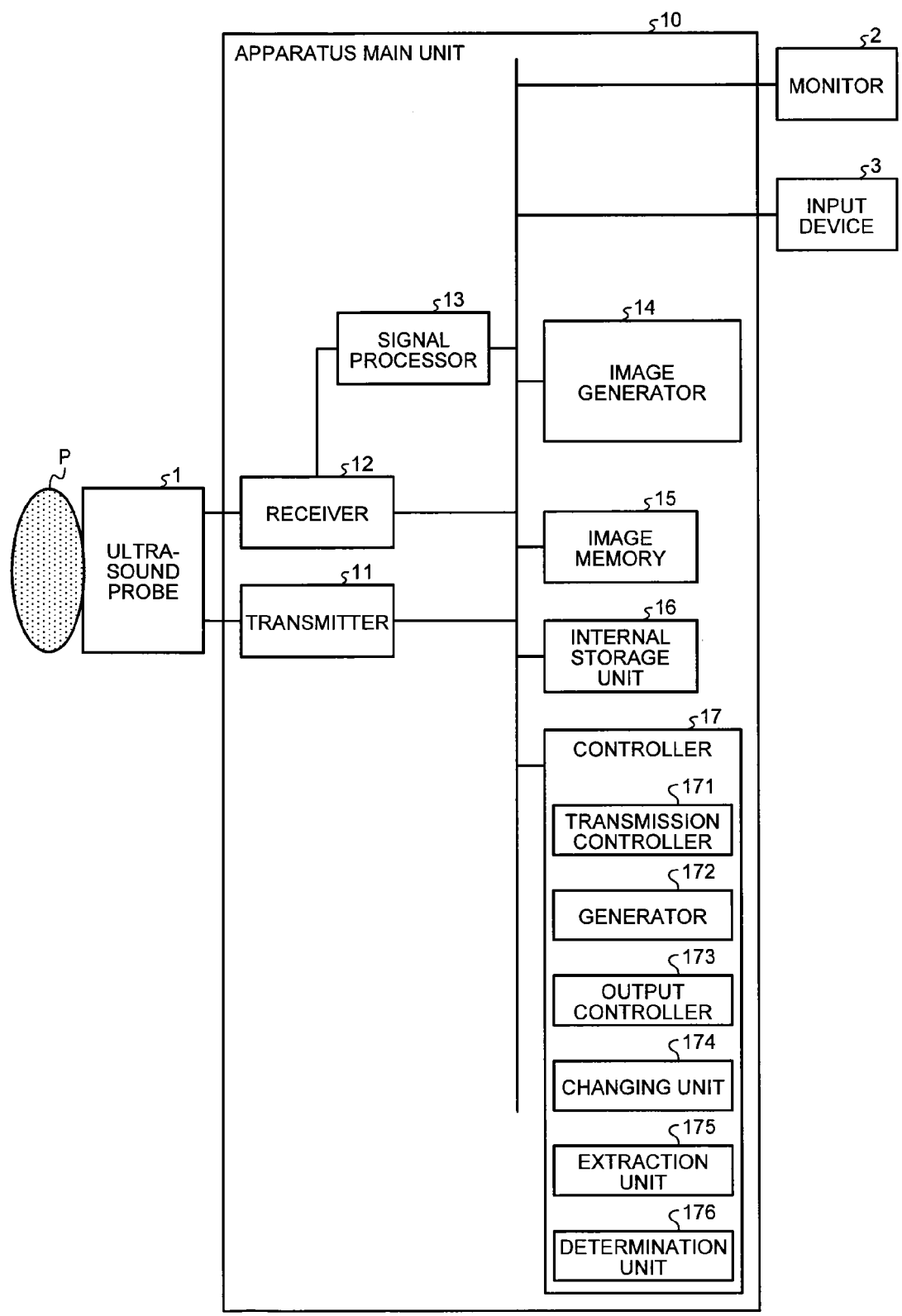
FIG. 6 is a block diagram of an exemplary configuration of an ultrasound diagnosis apparatus according to a second embodiment.

FIG. 6 is a block diagram of an exemplary configuration of an ultrasound diagnosis apparatus according to the second embodiment. The ultrasound diagnosis apparatus according to the second embodiment has the same configuration as that of the ultrasound diagnosis apparatus shown in FIG. 1 but is different from the ultrasound diagnosis apparatus shown in FIG. 1 in that the ultrasound diagnosis apparatus according to the second embodiment includes an extraction unit 175 and a determination unit 176 and that the processing performed by the output controller 173 and the changing unit 174 is different in part. For the second embodiment, the different aspects from the first embodiment will be described mainly and the same reference numerals as those used in FIG. 1 are used to denote the same functions as those of the configuration described for the first embodiment and descriptions for the same functions will not be given here.

The extraction unit 175 extracts the outline of body tissue from the ultrasound image data. The outline of body tissue is not limited to the outline of internal organs, such as the heart and lever, and includes the outline of various types of tissue that can be confirmed by sight in ultrasound image data. For example, the extraction unit 175 extracts an outline from the B-mode image data by using a technology for extracting the edge from image data.

On the basis of the outline and a transmission position, the determination unit 176 determines whether there is a given outline within a given area from the transmission position. For example, the determination unit 176 determines whether there is a structure boundary that may cause reflected shear waves that propagate in the same direction as that of shear waves near the burst wave transmission position.

The output controller 173 has the same functions as those described for the first embodiment. Furthermore, the output controller 173 outputs a warning when it is determined that there is a given outline within a given area. For example, the output controller 173 displays a warning message on the monitor 2 or outputs a warning sound via a speaker.

The changing unit 174 has the same functions as those described for the first embodiment. Furthermore, when it is determined that there is the given outline within the given area, the changing unit 174 changes at least one of the position to which the transmitter 11 transmits displacement-causing burst waves, the number of transmission positions, the position of scanning area, the area of scanning area, and the number of scanning areas. For example, the changing unit 174 changes the burst wave transmission position until no structure boundary that may cause reflected shear waves that propagate in the same direction as that of shear waves exists near the burst wave transmission position. In accordance with the change of the burst wave transmission position, the changing unit 174 changes other parameters, such as the number of positions to which displacement-causing burst waves are transmitted, the position of scanning area, the area of scanning area, and the number of scanning areas on the basis of the offset value and the upper limit value of the ROI width.

Figure 7:
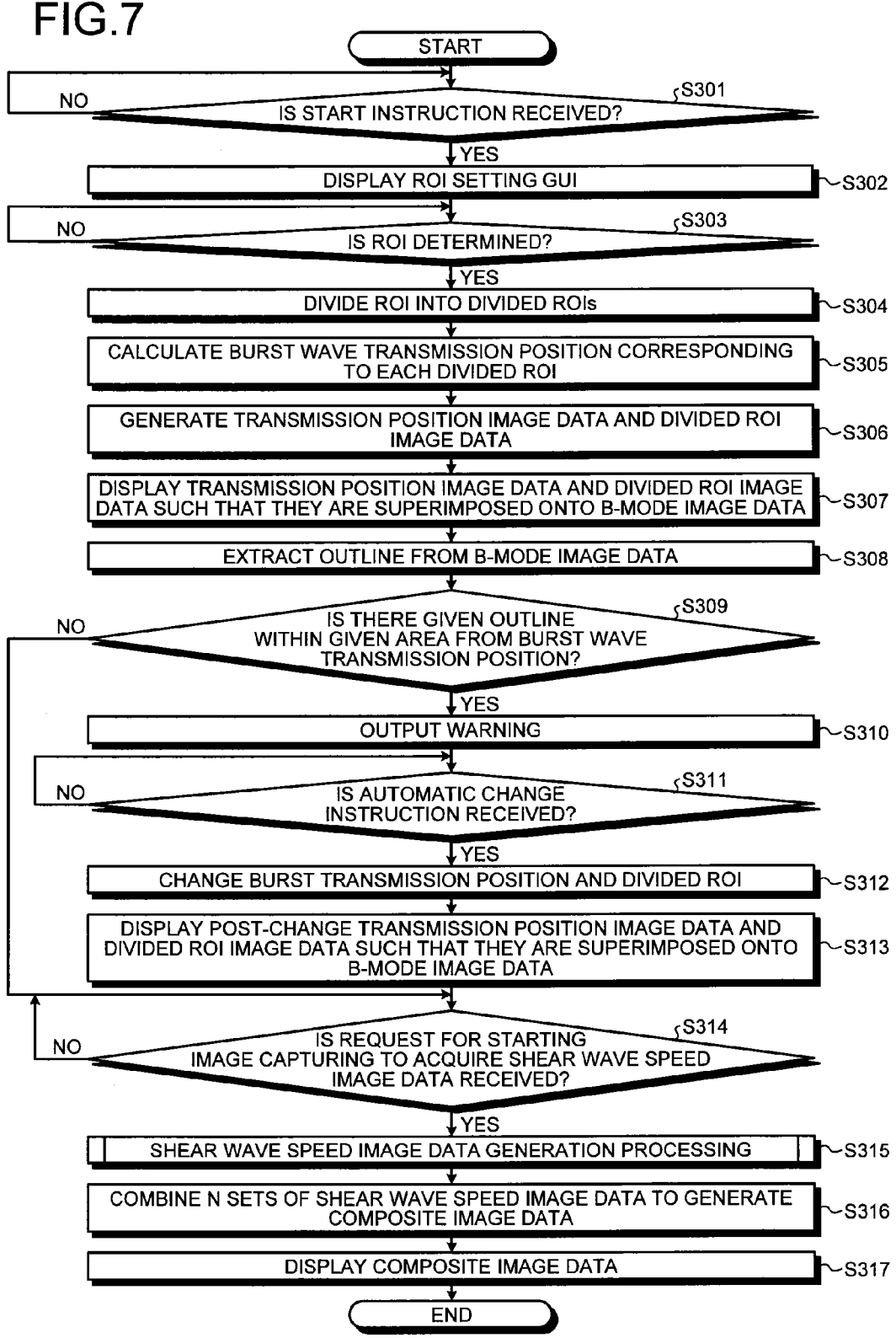
FIG. 7 is a flowchart of a procedure taken by the ultrasound diagnosis apparatus according to the second embodiment.
Figure 8:
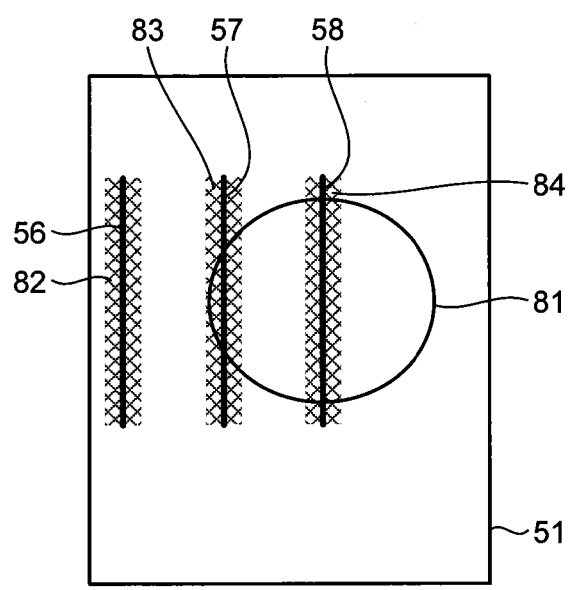
FIG. 8 illustrates processing performed by the ultrasound diagnosis apparatus according to the second embodiment.
Figure 9A:
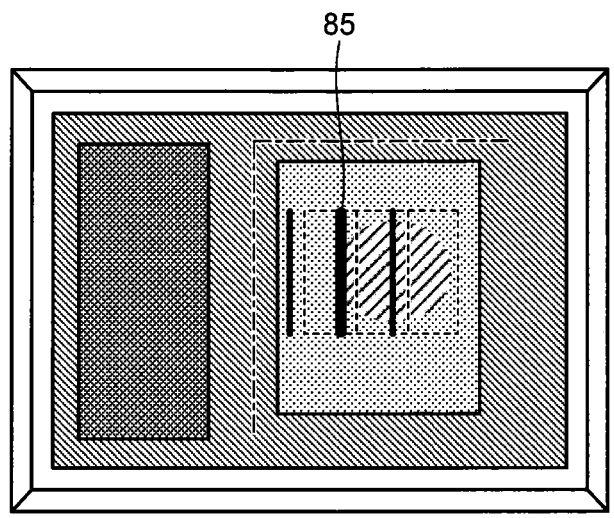
FIGS. 9A and 9B illustrate processing performed by the ultrasound diagnosis apparatus according to the second embodiment.
Figure 9B:
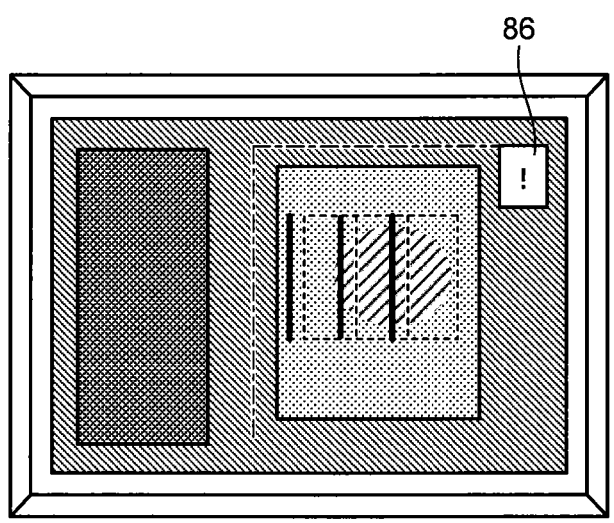

FIG. 7 is a flowchart of a procedure taken by the ultrasound diagnosis apparatus according to the second embodiment. With reference to FIGS. 8, 9A, and 9B, the procedure taken by the ultrasound diagnosis apparatus according to the second embodiment will be described below. FIGS. 8, 9A and 9B illustrate processing performed by the ultrasound diagnosis apparatus according to the second embodiment.

As illustrated in FIG. 7, the processing from step S301 to step S307 is the same as the processing from step S101 to step S107 illustrated in FIG. 4A and thus the descriptions thereof will be omitted here. In other words, the processing until the exemplary display image shown in FIG. 5B is displayed is the same as that of the first embodiment.

The extraction unit 175 extracts the outline from the B-mode image data (step S308). The processing performed by the extraction unit 175 will be described with reference to FIG. 8. As shown in FIG. 8, the extraction unit 175 extracts an outline 81 of a structure from the B-mode image 51 shown in FIG. 5B. Many methods have been already proposed for the method of extracting an outline from an image and are widely used for B-mode images (ultrasound images). For example, the extraction unit 175 extracts the outline 81 of the oval hatched area shown in FIG. 5B from the B-mode image 51 by using the technology disclosed in Japanese Laid-open Patent Publication No. 2010-282268. The B-node image 51 is shown as a white area and the outline 81 is shown on the image as a matter of convenience. However, practically, an image of the outline 81 can be displayed such that the outline 81 is superimposed on onto the arbitrary B-mode image 51 displayed on the monitor 2. Furthermore, the outline 81 is not necessarily superimposed onto the arbitrary B-mode image 51 when displayed. For example, when shear wave speed image data has been captured, the outline 81 may be displayed such that the outline 81 is superimposed onto the shear speed image data. The case has been described here where the extraction unit 175 extracts the single outline 81. Alternatively, the extraction unit 175 may extract multiple outlines. The extraction unit 175 stores the information on a single outline or multiple outlines in the internal storage unit 16.

The determination unit 176 determines whether there is a given outline within a given area from the burst wave transmission position (step S309). The given area is, for example, an area of 0.3 cm or less from the burst wave transmission position. The given outline is, for example, an outline including a tangent parallel to the burst wave transmission position. If it is not parallel to the beams of displacement-causing burst waves, there are little effects on propagation of shear waves.

The processing performed by the determination unit 176 will be described with reference to FIG. 8. For example, the determination unit 176 compares the position of the outline 81 that is extracted by the extraction unit 175 and the displayed burst wave transmission position and determines whether the outline 81 is within the area of 0.3 cm from the burst wave transmission position. For example, in the example shown in FIG. 8, the determination unit 176 sets areas 82, 83, and 84 having a width of 0.3 cm on the right and left with respect to the respective burst wave transmission positions 56, 57, and 58, i.e., having a width of 0.6 cm and whose centers are at the burst wave transmission positions, respectively. The determination unit 176 determines whether the areas 82, 83, and 84 include the outline 81. In the example shown in FIG. 8, the determination unit 176 determines that the areas 83 and 84 include the outline 81. The determination unit 176 then determines whether the outline 81 within the area 83 includes a tangent parallel to the burst wave transmission position and whether the outline 81 within the area 84 includes a tangent parallel to the burst wave transmission position. In the example shown in FIG. 8, the determination unit 176 determines that the outline 81 within the area 83 includes a tangent parallel to the burst wave transmission position 57 and determines that the outline 81 within the area 84 does not include a tangent parallel to the burst wave transmission position 58. Accordingly, the determination unit 176 determines whether there is a structure boundary that may cause reflected shear waves that propagate in the same direction as that of shear waves near the burst wave transmission position. The above-described given area and given outline are examples only and do not put any limits. For example, the given area may be changed to a value according to the operator's discretion. Furthermore, the given outline can be changed to an outline having an angle according to the operator's discretion.

When it is determined that there is not the given outline within the given area (NO at step S309), the procedure shifts the processing at step S314. On the other hand, when it is determined that there is the given outline within the given area (YES at step S309), the output controller 173 outputs a warning (step S310). For example, the output controller 173 displays a warning message on the monitor 2 or outputs warning sound via a speaker. For example, as shown in FIG. 9A, the output controller 173 displays the burst wave transmission position 57, regarding which it is determined that there is the given outline within the given area from the burst wave transmission position, in a wider line than those of other burst wave transmission positions 56 and 58. For example, as shown in FIG. 9B, the output controller 173 displays a caution mark 86 on the upper right on the screen of the monitor 2. This does not limit examples of the warning that is output by the output controller 173. For example, a line 85 shown in FIG. 9A may be displayed in a color different from that of other burst wave transmission positions.

The following descriptions refer back to FIG. 7. The changing unit 174 determines whether an automatic change instruction that is an instruction for automatically changing the burst wave transmission position and divided ROI is received from the operator (step S311). When no automatic change instruction is received (NO at step S311), the changing unit 174 waits until an automatic change instruction is received.

When an automatic change instruction is received (YES at step S311), the changing unit 174 changes the burst wave transmission position and the divided ROI (step S312). For example, the changing unit 174 shifts the burst wave transmission position 57 leftward such that the outline 81 cannot be within an area of 0.3 cm from the burst wave transmission position 57. As described for the first embodiment, on the basis of the offset value and the upper limit value of the ROI width, the changing unit 174 changes other parameters, such as the number of positions to which displacements-causing burst waves are transmitted, the position of scanning area, the area of scanning area, and the number of scanning areas. Accordingly, as illustrated in FIG. 5D, the changing unit 174 changes the burst wave transmission position such that the given outline is not close to the burst wave transmission position. The embodiments are not limited to the above-described example. For example, the changing unit 174 may shift the burst wave transmission position 57 rightward.

The processing from step S313 to step S317 is the same as the processing from step S109 to step S113 and thus the descriptions thereof will be omitted here.

Embodiments are not limited to the above-described procedure. For example, the processing for outputting a warning (step S310) is not necessarily performed. In this case, for example, when it is determined the given outline is within the given area (YES at step S309), the changing unit 174 automatically changes the burst wave transmission position and the divided ROI (step S312).

For example, such automatically changing processing (step S311 and step S312) is not necessarily performed. In this case, for example, as described for the first embodiment, the changing unit 174 changes the burst wave transmission position and divided ROI according to the change instructions from the operator.

As described above, the ultrasound diagnosis apparatus according to the second embodiment determines whether there is a structure boundary near a burst wave transmission position. Upon determining that there is a structure boundary near the burst wave transmission position, the ultrasound diagnosis apparatus outputs a warning. Accordingly, the ultrasound diagnosis apparatus according to the second embodiment can make a notification indicating whether displacement-causing burst waves are to be transmitted in the vicinity of the structure boundary while the operator does not confirm the displayed burst wave transmission position and B-mode image by sight in detail.

The ultrasound diagnosis apparatus according to the second embodiment automatically changes the burst wave transmission position and divided ROI upon determining that there is a structure boundary near the burst wave transmission position. Accordingly, the ultrasound diagnosis apparatus according to the second embodiment can optimize the burst wave transmission position and the position of the divided ROI without additional operation by the operator. The operator can confirm the optimized burst wave transmission position and position of the divided ROI and then practically start generating and displaying shear wave speed image. For example, upon determining that there is a structure boundary near the burst wave transmission position, the ultrasound diagnosis apparatus according to the second embodiment may make a setting such that processing for generating and displaying shear wave speed image is not performed. In this case, for example, the controller 17 controls the transmission controller 171 not to collect images even if an image capturing request for acquiring shear wave speed image data is received. Accordingly, the ultrasound diagnosis apparatus according to the second embodiment can avoid image generation in a situation where an artifact due to reflection of shear waves may occur.

For the second embodiment, the case has been describe where the extraction unit 175 extracts an outline. Alternatively, the extraction unit 175 may extract the surface of bone or a structure such as plaque or tumor that may rupture. Accordingly, the operator can easily know whether displacement-causing burst waves are to be transmitted to a part regarding which ultrasound signal transmission having a great acoustic energy should be avoided.

Third Embodiment

For the first and second embodiments, the case has been described where, after it is determined whether there is a structure boundary near a burst wave transmission position, the burst wave transmission position and divided ROI are changed and shear wave speed image data is acquired by image capturing. However, embodiments are not limited to this. For example, after shear wave speed image data is acquired by image capturing, the ultrasound diagnosis apparatus may generate reach time color image data corresponding to the time at which shear waves reach in order to confirm whether proper shear wave propagation occurs during the image capturing. For the third embodiment, a case will be described where an ultrasound diagnosis apparatus generates reach time color image data.

The ultrasound diagnosis apparatus according to the third embodiment has the same configuration as that of the ultrasound diagnosis apparatus shown in FIG. 1 but is different from the ultrasound diagnosis apparatus shown in FIG. 1 in a part of the processing performed by the image generator 14 and the output controller 173. Thus, for the third embodiment, the different aspects from the first embodiment will be described mainly and the same reference numerals as those used in FIG. 1 are used to denote the same functions as those of the configuration described for the first embodiment and descriptions for the same functions will not be given here.

The image generator 14 generates reach time color image data displaying the times at which shear waves reach. The reach time color image data is, for example, image data obtained by plotting, in each point in a scanning area, a pixel value corresponding to the time at which shear waves reach each point. For example, the image generator 14 generate reach time color image data by plotting, in each point in the scanning area, a color corresponding to the time at which shear waves reach each point in the scanning area.

The output controller 173 displays the reach time color image data. For example, the output controller 173 displays the reach time color image data, which is generated by the image generator 14, such that the reach time color image data is superimposed onto the B-mode image data.

Figure 10:
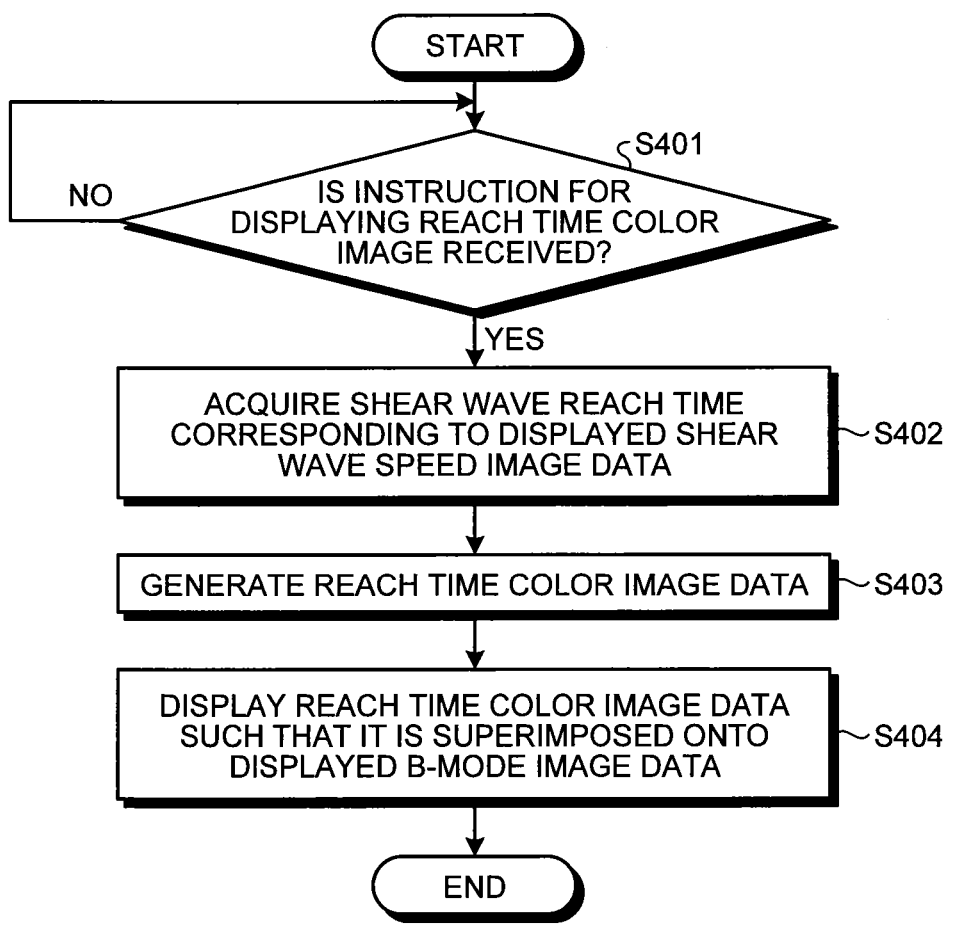
FIG. 10 is a flowchart of a procedure taken by an ultrasound diagnosis apparatus according to a third embodiment.
Figure 11A:
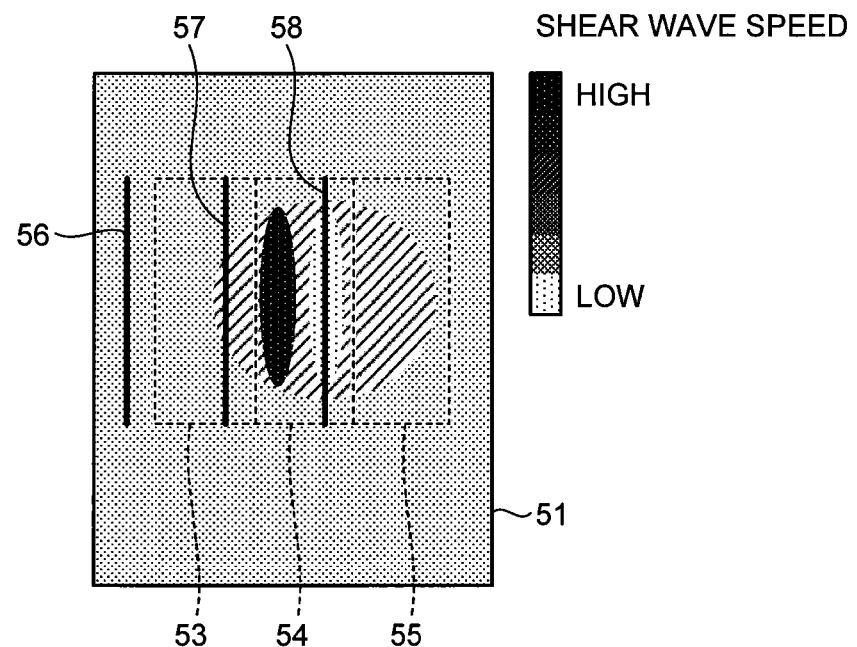
FIGS. 11A and 11B illustrate processing performed by the ultrasound diagnosis apparatus according to the third embodiment.
Figure 11B:
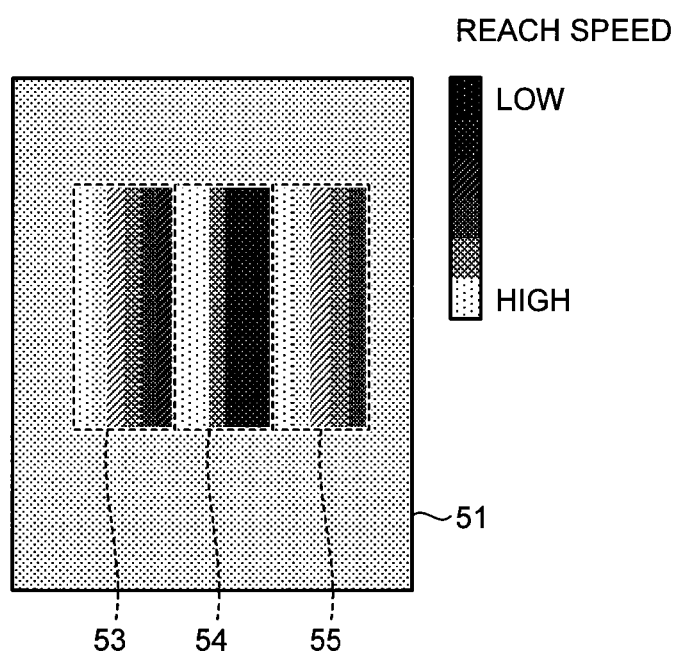

FIG. 10 is a flowchart of a procedure taken by the ultrasound diagnosis apparatus according to the third embodiment. The procedure taken by the ultrasound diagnosis apparatus according to the third embodiment will be described below with reference to FIGS. 11A and 11B. FIGS. 11A and 11B illustrate processing performed by the ultrasound diagnosis apparatus according to the third embodiment.

Here, a case will be described where the display image shown in FIG. 11A is displayed on the monitor 2 according to the processing of the first embodiment. The display image contains the B-mode image 51, and the divided ROIs 53, 54, and 55 where shear wave speed images are displayed, respectively. It is represented that the shear wave speed in the oval structure on the B-mode image 51 shown in FIG. 11A is roughly higher than that of the surrounding tissue and parts of irregularly different shear wave speeds can be seen in the divided ROI 54. The operator cannot determine, only by watching the display image shown in FIG. 11A, whether the parts accurately reflect the hardness of tissue or the parts result from improper detection of shear wave propagation. For this reason, the ultrasound diagnosis apparatus according to the third embodiment generates and displays reach time color image data.

As shown in FIG. 10, the image generator 14 of the ultrasound diagnosis apparatus according to the third embodiment determines whether a display instruction for displaying reach time color image data is received from the operator (step S401). When no display instruction is received (NO at step S401), the image generator 14 waits until a display instruction is received.

The image generator 14 acquires, from the internal storage unit 16, the times at which shear waves reach corresponding to the displayed shear wave image data (step S402). The internal storage unit 16 stores, for example, information on the shear wave speed image data that is acquired by image capturing.

The image generator 14 uses the acquired reach times to generate reach time color image data (step S403). For example, the image generator 14 generates reach time color image data by plotting, in each point in the scanning area, a color corresponding to the time at which shear waves reach each point in the scanning area. The reach time used here is not limited to the maximum value of displacement. For example, the reach time may be a maximum value of change of displacement over time. Alternatively, the difference between laterally adjacent two points may be calculated by calculating a cross-correlation between time-displacement curves of the two points and the calculated values may be summed from the value of the position where displacement is caused to acquire a reach time at each point.

The output controller 173 then displays the reach time color image data, which is generated by the image generator 14, such that the reach time color image data is superimposed onto the displayed B-mode image data (step S404). FIG. 11B shows exemplary reach time color image data that is displayed by the output controller 173. In this case, shear waves are generated on the left of each of the divided ROIs 53, 54, and 55 and the shear waves propagate rightward. For this reason, if the reach time increases from the left to the right in each divided ROI, it can be determined that propagating shear waves are properly detected. In other words, it is expected that the color changes to be deep from the left to the right in each divided ROI. However, in the example shown in FIG. 11B, while such an expected color change can be seen in the divided ROI 53 and the divided ROI 55, the color suddenly changes in the divided ROI 54 (i.e., the middle color cannot be seen), which indicates that shear waves that move rightward cannot be detected properly.

As described above, the ultrasound diagnosis apparatus according to the third embodiment generates and displays reach time color image data. Accordingly, with the ultrasound diagnosis apparatus according to the third embodiment, after confirming by sight burst wave transmission positions on the B-mode image 51, the operator can easily confirm whether shear waves are generated and propagate as expected. For example, when an artifact occurs in a shear wave speed image due to reflection or refraction of shear waves, the cause of the artifact can be identified and it can be determined easily whether the structure displayed on the sheer wave speed image accurately reflects the structure in the patient. Furthermore, when the operator moves the ultrasound probe 1 or changes the burst wave transmission positions individually, the operator can confirm each time how the manipulation influences the shear wave propagation and highly-reliable shear wave speed image data is generated and accordingly the data can be easily reflected to the manipulation. The divided ROI 54 shown in FIG. 11B indicates that shear waves that move rightward are not properly detected. In this case, for example, by switching the display screen on the monitor 2 to the display image shown in FIG. 5B, the operator can confirm the distance between the burst wave transmission position 57 corresponding to the divided ROI 54 (or the position of the divided ROI 54) and the oval structure boundary. Furthermore, by experiencing the above-described confirmation when shear waves are not caused and propagate as expected, the operator can learn a proper distance between the burst wave transmission position 57 and the oval structure boundary, i.e., a distance with which an artifact tends not to occur.

For the third embodiment, the case has been described where, according to the processing of the first embodiment, the display image shown in FIG. 11A is displayed on the monitor 2. Alternatively, for example, the processing according to the third embodiment may be performed according to and the processing of the second embodiment when the display image shown in FIG. 11A is displayed on the monitor 2.

Alternatively, by combining the third embodiment and the first embodiment, the shear wave speed image and the reach time color image may be displayed simultaneously in parallel. Alternatively, the third embodiment and the second embodiments may be combined and, when a given outline is extracted near a burst wave transmission position, a warning may be output and a burst wave transmission position may be optimized.

Fourth Embodiment

For the first to third embodiments, the case has been described where, after the burst wave transmission positions and divided ROIs are displayed, the burst wave transmission positions and divided ROIs are changed or shear wave speed image data is acquired by image capturing. However, embodiments are not limited to this. For example, the ultrasound diagnosis apparatus may change the burst wave transmission positions and divided ROIs before displaying the burst wave transmission positions and divided ROIs. For a fourth embodiment, a case will be described where, before displaying the burst wave transmission positions and divided ROIs, an ultrasound diagnosis apparatus changes the burst wave transmission positions and divided ROIs.

The ultrasound diagnosis apparatus according to the fourth embodiment has the same configuration as that of the ultrasound diagnosis apparatus shown in FIG. 6 but is different from the ultrasound diagnosis apparatus shown in FIG. 6 in the procedure taken by the ultrasound diagnosis apparatus. Thus, for the fourth embodiment, the different aspects from the second embodiment will be described mainly and the same reference numerals as those used in FIG. 6 are used to denote the same functions as those of the configuration described for the second embodiment and descriptions for the same functions will not be given here.

FIG. 12 is a flowchart of a procedure taken by the ultrasound diagnosis apparatus according to the fourth embodiment. The processing from step S501 to step S505 shown in FIG. 12 is the same as the processing from step S101 to step S105 shown in FIG. 4A and thus descriptions thereof will not be given here. Furthermore, the processing from step S506 to step S510 is the same as the processing from step S308 to step S312 shown in FIG. 7 and thus descriptions thereof will not be given here.

The generator 172 then generates transmission position image data and divided ROI image data (step S511). For example, the generator 172 generates transmission position image data displaying the burst wave transmission positions that are changed by the changing unit 174 and divided ROI image data displaying the changed positions of the divided ROIs.

The output controller 173 displays the transmission position image data and divided ROI image data such that the transmission position image data and divided ROI image data are superimposed onto B-mode image data (step S512). The following processing from step S513 to step S516 is the same as the processing from step S110 to step S113 and thus descriptions thereof will not be given here.

Embodiments are not limited to the above-described procedure. For example, the processing for outputting a warning (step S508) is not necessarily performed. In this case, when it is determined that there is a given outline within a given area (YES at step S507), the changing unit 174 automatically changes the burst wave transmission positions and divided ROIs (step S510).

Furthermore, for example, automatic change processing is not necessarily performed (step S509 and step S510). In this case, for example, the changing unit 174 changes the burst wave transmission positions and divided ROIs according to change instructions from the operator as illustrated for the first embodiment.

Furthermore, processing for clearly displaying the transmission position image data and divided ROI image data on a screen (steps S511 and S512) is not necessarily performed. In this case, for example, any one of or both of transmission position image data and divided ROI image data is not necessarily generated and displayed.

As described above, the ultrasound diagnosis apparatus according to the fourth embodiment changes the burst wave transmission positions and divided ROIs before displaying the burst wave transmission positions and divided ROIs. Accordingly, without operator's confirming by sight of displayed burst wave transmission positions and the B-mode image in detail, the ultrasound diagnosis apparatus according to the fourth embodiment can optimize the burst wave transmission positions and divided ROIs and then generate and display a shear wave speed image.

For the above-described embodiments, the case has been illustrated where transmission position image data is superimposed onto an ultrasound image, such as a B-mode image. However, embodiments are not limited to this. For example, the output controller 173 may superimpose the generated transmission position image data and scanning area image data onto various types of medical image data that is acquired by image capturing by an X-ray diagnosis apparatus, and X-ray CT (Computed Tomography) apparatus, an MRI (Magnetic Resonance Imaging) apparatus, etc.

The components of each device illustrated in the drawings for the first to fourth embodiments are functional ideas and are not required to be configured physically as illustrated in the drawings. In other words, specific separation and integration between devices are not limited to those illustrated in the drawings and the devices may be configured in a way that they are entirely or partly separated or integrated functionally or physically according to various types of load or circumstances and according to an arbitrary unit. Furthermore, a part or all of the processing functions implemented by the devices may be implemented by the CPU or a program that is analyzed and executed by the CPU or may be implemented as wired-logic hardware. Each set of processing performed by the ultrasound diagnosis apparatus illustrated for the first to fourth embodiments can be performed by executing a prepared ultrasound imaging program. The ultrasound imaging program may be distributed via a network, such as the Internet. The ultrasound imaging program may be recorded in a computer-readable non-temporary recording medium, such as a hard disk, flexible disk (FD), CD-ROM, MO, or DVD, and may be read from the non-temporary recording medium and executed by a computer.

According to at least one of the above-described embodiments, the image quality of a hardness image can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
an ultrasound probe configured to:
    transmit a push pulse that causes a shear wave in a body tissue, and
    transmit a tracking pulse for observing displacement caused by the shear wave in a measurement area; and
processing circuitry configured to:
    acquire medical image data of a region including the measurement area and a transmission area where the push pulse is transmitted,
    extract a structure in the medical image data; and
    output a warning when a distance between the structure and the transmission area is less than or equal to a threshold.

2. An ultrasound diagnosis apparatus comprising:
an ultrasound probe configured to:
    transmit a push pulse that causes a shear wave in a body tissue based on a first transmission parameter, and
    transmit a tracking pulse for observing displacement caused by the shear wave in a measurement area based on a second transmission parameter; and
processing circuitry configured to:
    acquire medical image data of a region including the measurement area and a transmission area where the push pulse is transmitted,
    extract a structure in the medical image data; and
    determine at least one of the first transmission parameter and the second transmission parameter based on a position of the structure.

3. The ultrasound diagnosis apparatus according to claim 2, wherein the processing circuitry outputs transmission area image data displaying the transmission area that is changed according to the transmission parameter determined such that the transmission area image data is superimposed onto the medical image data.

4. An ultrasound diagnosis apparatus comprising:
an ultrasound probe configured to:
    transmit a push pulse that causes a shear wave in a body tissue, and
    transmit a tracking pulse for observing displacement caused by the shear wave in a measurement area; and
processing circuitry configured to:

acquire medical image data of a region including the measurement area and a transmission area where the push pulse is transmitted;

extract a structure in the medical image data, and monitor a positional relationship between the structure and the transmission area.

5. The ultrasound diagnosis apparatus according to claim 4, wherein the processing circuitry changes, when determined that the structure is located within the given distance from the transmission area according to the positional relationship monitored, at least any one of the transmission area, the number of transmission areas, a position of the measurement area corresponding to the transmission area, an area of the measurement area, and the number of measurement areas, and the ultrasound probe transmits the push pulse and the tracking pulse according to at least any one of the transmission area, the number of transmission areas, the position of the measurement area, the area of the measurement area, and the number of measurement areas.

6. The ultrasound diagnosis apparatus according to claim 4, wherein the processing circuitry outputs a warning when determined that the structure is located within the given distance from the transmission area according to the positional relationship monitored.

7. The ultrasound diagnosis apparatus according to claim 5, wherein the processing circuitry:

generates linear image data displaying the changed transmission area; and outputs the generated linear image data such that the linear image data is superimposed onto the medical image data.

8. The ultrasound diagnosis apparatus according to claim 4, wherein the processing circuitry:

generates reach time image data displaying a time at which shear waves reach, and causes the display to display the reach time image data.

* * * * *